US008617514B2

(12) United States Patent (10) Patent No.: US 8,617,514 B2
Chang et al. (45) Date of Patent: Dec. 31, 2013

(54) TUMOR-TARGETED NANODELIVERY SYSTEMS TO IMPROVE EARLY MRI DETECTION OF CANCER

(75) Inventors: Esther H. Chang, Potomac, MD (US); Kathleen F. Pirollo, Rockville, MD (US)

(73) Assignee: Georgetown University, Washington, DC (US)

(*) Notice: Subject to any disclaimer, the term of this patent is extended or adjusted under 35 U.S.C. 154(b) by 1144 days.

(21) Appl. No.: 11/583,708

(22) Filed: Oct. 20, 2006

(65) Prior Publication Data

US 2007/0134154 A1 Jun. 14, 2007

Related U.S. Application Data

(63) Continuation-in-part of application No. 10/113,927, filed on Apr. 2, 2002, which is a continuation-in-part of application No. 09/914,046, filed as application No. PCT/US00/04392 on Feb. 22, 2000, now Pat. No. 7,479,276.

(60) Provisional application No. 60/121,133, filed on Feb. 22, 1999, provisional application No. 60/280,134, filed on Apr. 2, 2001, provisional application No. 60/728,303, filed on Oct. 20, 2005.

(51) Int. Cl.
*A61K 51/12* (2006.01)
*A61K 49/04* (2006.01)
*A61K 49/06* (2006.01)
*A61K 49/18* (2006.01)
*A61K 39/00* (2006.01)
*A61K 9/127* (2006.01)
*A61K 35/00* (2006.01)
*A61K 35/04* (2006.01)
*A61B 5/055* (2006.01)
*A61B 8/00* (2006.01)
*C07K 16/00* (2006.01)

(52) U.S. Cl.
USPC ....... 424/1.21; 424/9.3; 424/9.321; 424/9.34; 424/9.4; 424/9.5; 424/9.51; 424/178.1; 424/450; 514/19.2; 514/19.3

(58) Field of Classification Search
None
See application file for complete search history.

(56) References Cited

U.S. PATENT DOCUMENTS

| 5,688,488 | A | 11/1997 | Low et al. |
| 6,251,365 | B1 | 6/2001 | Bauerlein et al. |
| 2002/0146371 | A1* | 10/2002 | Li et al. ........................ 424/1.73 |
| 2003/0044407 | A1 | 3/2003 | Chang et al. |
| 2007/0065499 | A1 | 3/2007 | Chang et al. |

FOREIGN PATENT DOCUMENTS

| JP | 09-110722 | 4/1997 |
| JP | A-2001-527534 | 12/2001 |
| WO | WO 97/28817 | 8/1997 |
| WO | WO 99/25320 | 5/1999 |
| WO | WO 00/50008 | 8/2000 |
| WO | WO 00/50008 A2 * | 8/2000 |
| WO | WO 01/82899 | 11/2001 |
| WO | WO 02/078608 A2 * | 10/2002 |
| WO | WO 03/084386 | 10/2003 |
| WO | WO 2004/066946 | 8/2004 |
| WO | WO 2005/000271 | 1/2005 |
| WO | WO 2005/016141 | 2/2005 |

OTHER PUBLICATIONS

Steeg and Theodorescu (Nature Clin. Practice Oncol. 2008, 16 pages, medscape.com/viewarticle/571455_print).*
Niesman et al (J. Liposome Res. 4(2): 741-768, 1994).*
Torchlin (Molec. Med. Today, Jun. 1996, 242-249).*
Pirollo et al (Molecular Imaging 1/06, 5(1): 41-52).*
Wang, P. (A Training Program in Breast Cancer Research Using NMR Techniques, Report Date: Jul. 2005, pp. 1-69).*
Alisauskus,R., et al., "Initial Studies of Monoclonal Antibody PAM4 Targeting to Xenografted Orthotopic Pancreatic Cancer," *Cancer Res.* 55:5743s-5748s, American Association for Cancer Research (1995).
Allen, T.M., et al., "A new strategy for attachment of antibodies to sterically stabilized liposomes resulting in efficient targeting to cancer cells," *Biochim. Biophys. Acta* 1237:99-108, Elsevier Science Inc. (1995).
Allen, T.M., et al., "Antibody-Targeted Stealth® Liposomes" in *Stealth Liposomes*, Lasic, D.D. and Martin, F.J., eds., CRC Press Inc., Boca Raton, FL, pp. 233-244 (1995).
Aoki, K., et al., "Liposome-mediated in Vivo Gene Transfer of Antisense K-*ras* Construct Inhibits Pancreatic Tumor Dissemination in the Murine Peritoneal Cavity," *Cancer Res.* 55:3810-3816, American Association for Cancer Research (1995).

(Continued)

*Primary Examiner* — Daniel E Kolker
*Assistant Examiner* — Marianne DiBrino
(74) *Attorney, Agent, or Firm* — Fanelli Haag & Kliger PLLC

(57) ABSTRACT

The present invention is in the fields of drug delivery, cancer treatment and diagnosis and pharmaceuticals. This invention provides a method of making antibody- or antibody fragment-targeted immunoliposomes for the systemic delivery of molecules to treat and image diseases, including cancerous tumors. The invention also provides immunoliposomes and compositions, as well as methods of imaging various tissues. The liposome complexes are useful for encapsulation of imaging agents, for example, for use in magnetic resonance imaging. The specificity of the delivery system is derived from the targeting antibodies or antibody fragments.

27 Claims, 20 Drawing Sheets

(56) References Cited

OTHER PUBLICATIONS

Bajoria, R. and Contractor, S.F., "Effect of Surface Charge of Small Unilamellar Liposomes on Uptake and Transfer of Carboxyfluorescein across the Perfused Human Term Placenta [Regular Articles]," *Pediatr. Res.* 42:520-527, International Pediatrics Research Foundation, Inc. (1997).

Bajoria, R., et al., "Endocytotic uptake of small unilamellar liposomes by human trophoblast cells in culture," *Hum. Reprod.* 12:1343-1348, European Society for Human Reproduction and Embryology (1997).

Batra, J.K., et al., "Single-Chain Immunotoxins Directed at the Human Transferrin Receptor Containing Pseudomonas Exotoxin A or Diphtheria Toxin: Anti-TFR(Fv)-PE40 and DT388-Anti-TFR(Fv)," *Mol. Cell. Biol.* 11:2200-2205, American Society for Microbiology (1991).

Bristow, R.G., et al., "The p53 gene as a modifier of intrinsic radiosensitivity: implications for radiotherapy," *Radiother. Oncol.* 40:197-223, Elsevier Scientific Publishers (1996).

Chen, L., et al., "Synergistic activation of p53 by inhibition of *MDM2* expression and DNA damage," *Proc. Natl. Acad. Sci. USA* 95:195-200, National Academy of Sciences (1998).

Cheng, P-W., "Receptor Ligand-Facilitated Gene Transfer: Enhancement of Liposome-Mediated Gene Transfer and Expression by Transferrin," *Hum. Gene Ther.* 7:275-282, Mary Ann Liebert, Inc. (1996).

Chiarugi, V., et al., "Cox-2, iNOS and p53 as play-makers of tumor angiogenesis (Review)," *Int. J. Mol. Med.* 2:715-719, D.A. Spandidos (1998).

Choi, Y.H., et al., "Characterization of a Targeted Gene Carrier, Lactose-Polyethylene Glycol-Grafted Poly-L-Lysine, and Its Complex with Plasmid DNA," *Human Gene Ther.* 10:2657-2665, Mary Aim Liebert, Inc. (1999).

Clark, P.R. and Hersh, E.M., "Cationic lipid-mediated gene transfer: Current concepts," *Curr. Opin. Mol. Ther.* 1:158-176, Current Drugs Ltd. (1999).

Cristiano, R.J. and Curiel, D.T., "Strategies to accomplish gene delivery via the receptor-mediated endocytosis pathway," *Cancer Gene Ther.* 3:49-57, Nature Publishing Group (1996).

Degani, H., et al., "Magnetic resonance imaging of tumor vasculature," *Thromb Haemost.* 89:25-33, Schattauer (2003).

Diebel, C.E., et al., "Magnetite defines a vertebrate magnetoreceptor," *Nature* 406:299-302, Macmillan Magazine Ltd. (2000).

Drummond, D.C., et al., "Optimizing Liposomes for Delivery of Chemotherapeutic Agents to Solid Tumors," *Pharmacol. Rev.* 51:691-743, The American Society for Pharmacology and Experimental Therapeutics (1999).

Dubé, D., et al., "Preparation and Tumor Cell Uptake of Poly(*N*-isopropylacrylamide) Folate Conjugates," *Bioconjugate Chem.* 13:685-692, American Chemical Society (2002).

Dunlap, D.D., et al., "Nanoscopic structure of DNA condensed for gene delivery," *Nucleic Acids Res.* 25:3095-3101, Oxford University Press (1997).

Elliott, R.L., et al., "Breast Carcinoma and the Role of Iron Metabolism: A Cytochemical, Tissue Culture, and Ultrastructural Study," *Ann. N.Y. Acad. Sci.* 698:159-166, New York Academy of Sciences (1993).

Felgner, P.L., et al., "Improved Cationic Lipid Formulations for In Vivo Gene Therapy," *Ann. N.Y. Acad. Sci.* 772:126-139, New York Academy of Sciences (1995).

Foo, J-J., et al., "Contact deformation of liposome in the presence of osmosis," *Ann. Biomed. Eng.* 31:1279-1286, Springer Science and Business Media (2003).

Forssen, E. and Willis, M., "Ligand-targeted liposomes," *Adv. Drug Deliv. Rev.* 29:249-271, Elsevier Science B.V. (1998).

Freedman, M., et al., "Ultrasound images of implanted tumors in nude mice using Sono-CT® correlated with MRI apperance," *Proc. SPIE* 4321:163-167, The International Society for Optical Engineering (2001).

Fujiwara, T., et al., "A Retroviral Wild-Type *p53* Expression Vector Penetrates Human Lung Cancer Spheroids and Inhibits Growth by Inducing Apoptosis," *Cancer Res.* 53:4129-4133, American Association for Cancer Research (1993).

Fujiwara, T., et al., "Induction of Chemosensitivity in Human Lung Cancer Cells in vivo by Adenovirus-mediated Transfer of the Wild-Type *p53* Gene," *Cancer Res.* 54:2287-2291, American Association for Cancer Research (1994).

Gershon, H., et al., "Mode of formation and structural features of DNA-cationic liposome complexes used for transfection," *Biochemistry* 32:7143-7151, American Chemical Society (1993).

Gillies, R.J., et al., "Applications of Magnetic Resonance in Model Systems: Tumor Biology and Physiology," *Neoplasia* 2:139-451, Nature America Inc. (2000).

Hamada, K., et al., "Adenovirus-mediated Transfer of a Wild-Type *p53* Gene and Induction of Apoptosis in Cervical Cancer," *Cancer Res.* 56:3047-3054, American Association for Cancer Research (1996).

Haynes, B.F., et al., "Characterization of a Monoclonal Antibody (5E9) that Defines a Human Cell Surface Antigen of Cell Activation," *J. Immunol.* 127:347-352, The Williams & Wilkins Co. (1981).

Huwyler, J., et al., "Brain drug delivery of small molecules using immunoliposomes," *Proc. Natl. Acad. Sci. USA* 93:14164-14169, National Academy of Sciences (1996).

Jain, R.K. and Baxter, L.T., "Mechanisms of Heterogenous Distribution of Monoclonal Antibodies and Other Macromolecules in Tumors: Significance of Elevated Interstitial Pressure," *Cancer Res.* 48:7022-7032, American Association for Cancer Research (1988).

Johnson, P., et al., "Expression of Wild-Type p53 Is Not Compatible with Continued Growth of p53-Negative Tumor Cells," *Mol. Cell Biol.* 11:1-11, American Society for Microbiology (1991).

Kawaura, C., et al., "Atomic force microscopy for studying gene transfection mediated by cationic liposome with a cationic cholesterol derivative," *FEBS Letts* 421:69-72, Federation of European Biochemical Societies (1998).

Keer, H.N., et al., "Elevated transferrin receptor content in human prostate cancer cell lines assessed in vitro and in vivo," *J. Urol.* 143:381-385, Lippincott Williams & Wilkins (1990).

Kerr, J.F.R., et al., "Apoptosis: Its Significance in Cancer and Cancer Therapy," *Cancer* 73:2013-2026, Wiley (1994).

Kirpotin, D., et al., "Sterically Stabilized Anti-HER2 Immunoliposomes: Design and Targeting to Human Breast Cancer Cells in Vitro," *Biochemistry* 36:66-75, American Chemical Society (1997).

Koning, G.A., et al., "Antiproliferative effect of immunoliposomes containing 5-fluorodeoxyuridine-dipalmitate on colon cancer cells," *Br. J. Cancer* 80:1718-1725, Cancer Research Campaign (1999).

Koning, G.A., et al., "Selective transfer of a lipophilic prodrug of 5-fluorodeoxyuridine from immunoliposomes to colon cancer cells," *Biochim. Biophys. Acta* 1420:153-167, Elsevier Science B.V. (1999).

Konishi, H., et al., "Targeting Strategy for Gene Delivery to Carcinoembryonic Antigen-Producing Cancer Cells by Retrovirus Displaying a Single-Chain Variable Fragment Antibody," *Hum. Gene Ther.* 9:235-248, Mary Ann Liebert, Inc. (1998).

Lasic, D.D., et al., "Sterically stabilized liposomes in cancer therapy and gene delivery," *Curr. Opin. Mol. Ther.* 1:177-185, Current Drugs Ltd. (1999).

Lasic, D.D., and Papahadjopoulous, D., "Liposomes Revisited," *Science* 267:1275-1276, American Association for the Advancement of Science (1995).

Laukkanen, M-L., et al., "Functional Immunoliposomes Harboring a Biosynthetically Lipid-Tagged Single-Chain Antibody," *Biochemistry* 33:11664-11670, American Chemical Society (1994).

Lee, R.J. and Huang, L., "Folate-targeted, Anionic Liposome-entrapped Polylysine-condensed DNA for Tumor Cell-specific Gene Transfer," *J. Biol. Chem.* 271:8481-8487, American Society for Biochemistry and Molecular Biology, Inc. (1996).

Lewis, J.G., et al., "A serum-resistant cytofectin for cellular delivery of antisense oligodeoxynucleotides and plasmid DNA," *Proc. Natl. Acad. Sci. USA* 93:3176-3181, National Academy of Sciences (1996).

(56) References Cited

OTHER PUBLICATIONS

Li, S. and Huang, L., "Functional Pleomorphism of Liposomal Gene Delivery Vectors—Lipoplex and Lipopolyplex," in *Liposomes—Rational Design*, Janoff, A.S., ed., Marcel Dekker, Inc., New York, NY, pp. 89-124 (1998).

Liu, T.J., et al., "Growth Suppression of Human Head and Neck Cancer Cells by the Introduction of a Wild-Type *p53* Gene via a Recombinant Adenovirus," *Cancer Res.* 54:3662-3667, American Association for Cancer Research (1994).

Lowe, S.W., "Cancer therapy and *p53*," *Curr. Opin. Oncol.* 7:547-553, Rapid Science Publishers (1995).

MaClean, A.L., et al., "Immunoliposomes as targeted delivery vehicles for cancer therapeutics (Review)," *Int. J. Oncol.* 11:325-332, International Journal of Oncology (1997).

Martin, F., et al., "Retroviral Vector Targeting to Melanoma Cells by Single-Chain Antibody Incorporation in Envelope," *Human Gene Ther.* 9:737-746, Mary Ann Liebert, Inc. (1998).

Massing, U., "Cancer therapy with liposomal formulations of anti-cancer drugs," *Int. J. Clin. Pharmacol. Ther.* 35:87-90, Dustri-Verlag Dr. K. Feistle (1997).

Matlashewski, G., "p53: Twenty years on, Meeting Review," *Oncogene Rev.* 18:7618-7620, Stockton Press (1999).

Miyamoto, T., et al., "Transferrin receptor in oral tumors," *Int. J. Oral Maxillofac. Surg.* 23:430-433, Munksgaard (1994).

Miyashita, T., et al., "Tumor suppressor p53 is a regulator of *bcl-2* and *bax* gene expression in vitro and in vivo," *Oncogene* 9:1799-1805, Macmillan Press Ltd. (1994).

Morawski, A.M., et al., "Targeted nanoparticles for quantitative imaging of sparse molecular epitotes with MRI," *Magn Reson Med* 51:480-486, Wiley-Liss, Inc. (Mar. 2004).

Nag, A., et al., "A Colorimetric Estimation of Polyethyleneglycol-Conjugated Phospholipid in Stealth Liposomes," *Anal. Biochem.* 250:35-43, Academic Press (1997).

Nam, S.M., et al., "Sterically stabilized anti-$G_{M3}$, anti-Le$^x$ immunoliposomes: targeting to B16BL6, HRT-18 cancer cells," *Oncol. Res.* 11:9-16, Cognizant Communication (1999).

Ng, K-Y., et al., "The effects of polyethyleneglycol (PEG)-derived lipid on the activity of target-sensitive immunoliposome," *Int. J. Pharma.* 193:157-166, Elsevier Science B.V. (2000).

Nicholson, I.C., et al., "Construction and Characterisation of a Functional CD19 Specific Single Chain Fv Fragment for Immunotherapy of B Lineage Leukaemia and Lymphoma," *Mol. Immunol.* 34:1157-1165, Elsevier Science Ltd. (1997).

Pagnan, G., et al.,"GD2-Mediated Melanoma Cell Targeting and Cytotoxicity of Liposome-Entrapped Fenretinide," *Int. J. Cancer* 81:268-274, Wiley-Liss, Inc. (1999).

Park, J.W., et al., "Development of anti-p185$^{HER2}$ immunoliposomes for cancer therapy," *Proc. Natl. Acad. Sci. USA* 92:1327-1331, National Academy of Sciences (1995).

Park, J.W., et al., "Tumor targeting using anti-her2 immunoliposomes," *J. Control. Rel.* 74:95-113, Elsevier Science B.V. (2001).

Pirollo, K.F., et al., "p53 mediated sensitization of squamous cell carcinoma of the head and neck to radiotherapy," *Oncogene* 14:1735-1746, Stockton Press (1997).

Pirollo, K.F., et al., "Immunoliposomes: A Targeted Delivery Tool for Cancer Treatment," in *Vector Targeting for Therapeutic Gene Delivery*, Curiel, D.T., and Douglas, J.T., eds., Wiley-Liss, Inc., Hoboken, NJ, pp. 33-62 (2002).

Ponka, P. and Lok, C.N., "The transferrin receptor: role in health and disease," *Intl. J. Biochem Cell Biol.* 31:1111-1137, Elsevier Science Ltd. (1999).

Poon, R.Y.M, "Advances in Monoclonal Antibody Applications: Bispecific Antibodies" in *Biotechnology International: International Developments in the Biotechnology Industry*, Fox, F., and Connor, T.H., eds., Universal Medical Press, Inc., San Francisco, CA, pp. 113-128 (1997).

Rait, A.S., et al., "Inhibitory effects of the combination of HER-2 antisense oligonucleotide and chemotherapeutic agents used for the treatment of human breast cancer," *Cancer Gene Ther.* 8:728-739, Nature Publishing Group (2001).

Rait, A., et al., "Tumor-targeting, Systemically Delivered Antisense HER-2 Chemosensitizes Human Breast Cancer Xenografts Irrespective of HER-2 Levels," *Mol Med.* 8:475-486, North Shore Long Island Jewish Research Institute (2002).

Rait, A., et al., "HER-2-Targeted Antisense Oligonucleotide Results in Sensitization of Head and Neck Cancer Cells to Chemotherapeutic Agents," *Ann. N.Y. Acad. Sci.* 1002:1-12, New York Academy of Sciences (2003).

Rasa, M., et al., "Atomic Force Microscopy and Magnetic Force Microscopy Study of Model Colloids," *J. Coll. Interface Sci* 250:303-315, Elsevier Science (2002).

Rossi, M.C. and Zetter, B.R., "Selective stimulation of prostatic carcinoma cell proliferation by transferrin," *Proc. Natl. Acad. Sci. (USA)* 89:6197-6201, National Academy of Sciences (1992).

Ruley, H.E., "p53 and Response to Chemotherapy and Radiotherapy," in *Important Adv. Oncol. 1996*, DeVita, V.T., et al., eds., Lippincott-Raven Publishers, Philadelphia, PA, pp. 37-56 (1996).

Schier, R., et al., "In vitro and in vivo characterization of a human anti-c-erbB-2 single-chain FV isolated from a filamentous phage antibody library," *Immunotechnology* 1:73-81, Elsevier Science B.V. (1995).

Sidransky, D. and Hollstein, M., "Clinical implications of the p53 gene," *Annu. Rev. Med.* 47:285-301, Annual Reviews, Inc. (1996).

Srivastava, S., et al., "Recombinant Adenovirus Vector Expressing Wild-type p53 is a Potent Inhibitor of Prostate Cancer Cell Proliferation," *Urology* 46:843-848, Excerpta Medica, Inc. (1995).

Suzuki, S., et al., "Modulation of doxorubicin resistance in a doxorubicin-resistant human leukaemia cell by an immunoliposome targeting transferring receptor," *Br. J. Cancer* 76:83-89, Cancer Research Campaign (1997).

The Journal of Gene Medicine Clinical Trials Database, "Gene Therapy Clinical Trials Worldwide," available online at w.wiley.co.uk/wileychi/genmed/clinical, John Wiley and Sons, Ltd., 2 pages (accessed Sep. 2001).

Thierry, A.R., et al., "Systemic gene therapy: Biodistribution and long-term expression of a transgene in mice," *Proc. Natl. Acad. Sci. USA* 92:9742-9746, National Academy of Science (1995).

Vertut-Doï, A., et al., "Binding and uptake of liposomes containing a poly(ethylene glycol) derivative of cholesterol (stealth liposomes) by the macrophage cell line J774: influence of PEG content and its molecular weight," *Biochim. Biophys. Acta* 1278:19-28, Elsevier Science B.V. (1996).

Volpert, O.V., et al., "Sequential development of an angiogenic phenotype by human fibroblasts progressing to tumorigenicity," *Oncogene* 14:1495-1502, Stockton Press (1997).

Weinberg, E.D., "Roles of Iron in Neoplasia: Promotion, Prevention, and Therapy," *Biol. Trace Element Res.* 34:123-140, Humana Press, Inc. (1992).

Winter, P.M., et al., Molecular Imaging of Angiogenesis in Early-Stage Atherosclerosis With $\alpha_v\beta_3$-Integrin-Targeted Nanoparticles, *Circulation* 108:2270-2274, American Heart Association, Inc. (2003).

Wisner, E.R., et al., "A Surface-Modified Chylomicron Remant-Like Emulsion for Percutaneous Computed Tomography Lymphography: Synthesis and Preliminary Imaging Findings," *Invest Radiol.* 37:232-239, Lippincott Williams & Wilkins, Inc. (2002).

Wright, S.E. and Huang, L., "Bilayer stabilization of phosphatidylethanolamine by N-biotinylphosphatidylethanolamine," *Biochim. Biophys. Acta* 1103:172-178, Elsevier Science B.V. (1992).

Wolfert, M.A., et al., "Characterization of Vectors for Gene Therapy Formed by Self-Assembly of DNA with Synthetic Block Co-Polymers," *Hum Gene Ther.* 7:2123-2133, Mary Ann Liebert, Inc. (1996).

Xu, L., et al.,"Systemic p53 Gene Therapy of Cancer with Immunolipoplexes Targeted by Anti-Transferrin Receptor scFv," *Mol Med.* 7:723-734, The Picower Institute Press (2001).

Xu, L., et al., "Systemic Tumor-targeted Gene Delivery by Anti-Transferrin Receptor scFv-Immunoliposomes," *Mol Cancer Ther.* 1:337-346, American Association for Cancer Research, Inc. (2002).

(56) References Cited

OTHER PUBLICATIONS

Xu, L., et al., "Self-Assembly of a Virus-Mimicking Nanostructure System for Efficient Tumor-Targeted Gene Delivery," *Hum. Gene Ther.* 13:469-481, Mary Ann Liebert, Inc. (2002).
Xu, L., et al.,"Transferrin-liposome-mediated systemic p53 gene therapy in combination with radiation results in regression of human head and neck cancer xenografts," *Hum Gene Ther.* 10:2941-2952, Mary Ann Liebert, Inc. (1999).
Xu, L., et al., "Systemic p53 gene therapy in combination with radiation results in human tumor regression," *Tumor Targeting* 4:92-104, Stockton Press (1999).
Yang, C., et al., "Adenovirus-mediated Wild-Type p53 Expression Induces Apoptosis and Suppresses Tumorigenesis of Prostatic Tumor Cells," *Cancer Res.* 55:4210-4213, American Association for Cancer Research (1995).
Yazdi, P.T. et al., "Infucence of Cellular Trafficking on Protein Synthesis Inhibition of Immunotoxins Directed against the Transferrin Receptor," *Cancer Res.* 55:3763-3771, American Association for Cancer Research (1995).
Yu, W., et al., Enhanced transfection efficiency of a systemically delivered tumor-targeting immunolipoplex by inclusion of a pH-sensitive histidylated oligolysine peptide, *Nucleic Acids Res.* 32: e48, Oxford University Press (2004).
Zhang, W-W., et al., "Advances in Cancer Gene Therapy," *Adv. Pharmacol.* 32:289-341, Academic Press, Inc. (1995).
Office Action in related co-pending U.S. Appl. No. 11/798,296 mailed Jan. 14, 2011.
Aigner, A.: "Delivery Systems for the Direct Application of siRNAs to Induce RNA Interference (RNAi) In Vivo", Journal of Biomedicine and Biotechnology, vol. 2006, Article ID 71659, pp. 1-15, 2006.
Kobstake, Elry, et al.: "A Fluoroimmunoassay Based on Immunoliposomes Containing Genetically Engineered Lipid-Tagged Antibody", Analytical Chemistry, vol. 69(7), pp. 1295-1298, 1997.
de Kruif, John, et al.: "Biosynthetically Lipid-Modified Human scFv Fragments From Phage Display Libraries as Targeting Molecules for Immunoliposomes", FEBS Letters 399, pp. 232-236, 1996.
Lesoon-Wood, Leslie A., et al.: "Systemic Gene Therapy with p53 Reduces Growth and Metastases of a Malignant Human Breast Cancer in Nude Mice", Human Gene Therapy, vol. 6, pp. 395-405, 1995.
Morishige, Hideaki, et al.: "In Vitro Cytostatic Effect of TNF (Tumor Necrosis Factor) Entrapped in Immunoliposomes on Cells Normally Insenstive to TNF", Biochimica et Biophysica Acta, vol. 1151, pp. 59-68, 1993.
Park, John W., et al.: "Immunoliposomes for Cancer Treatment", Advances in Pharmacology, vol. 40, pp. 399-435, 1997.
Simoes, S., et al.: "Enhancement of Cationic Liposome-Mediated Gene Delivery by Transferrin and Fusogenic Peptides", The 24th International Symposium on Controlled Release of Bioactive Materials, 24, pp. 659-660, 1997.
Thorstensen, Ketil, et al.: "The Transferrin Receptor: Its Diagnostic Value and its Potential as Therapeutic Target", Scandinavian Journal of Clinical and Laboratory Investigation, vol. 53 (Suppl 215), pp. 113-120, 1993.
Xu, Liang, et al.: "Transferrin-Liposome-Mediated p53 Sensitization of Squamous Cell Carcinoma of the Head and Neck to Radiation In Vitro", Human Gene Therapy, vol. 8, pp. 467-475, 1997.
DiBrino, M. Non-Final Office Action dated Sep. 22, 2005 issued in U.S. Appl. No. 10/113,927.
DiBrino, M. Non-Final Office Action dated Dec. 5, 2006 issued in U.S. Appl. No. 10/113,927.
DiBrino, M. Final Office Action dated Jul. 27, 2007 issued in U.S. Appl. No. 10/113,927.
DiBrino, M. Non-Final Office Action dated Feb. 7, 2008 issued in U.S. Appl. No. 10/113,927.
DiBrino, M. Final Office Action dated Nov. 25, 2008 issued in U.S. Appl. No. 10/113,927.
DiBrino, M. Notice of Allowance dated Mar. 23, 2010 issued in U.S. Appl. No. 10/113,927.
DiBrino, M., Non-Final Office Action dated Aug. 3, 2010 issued in U.S. Appl. No. 11/520,796.
DiBriino, M., Non-Final Office Action dated Apr. 28, 2010 issued in U.S. Appl. No. 11/798,296.

* cited by examiner

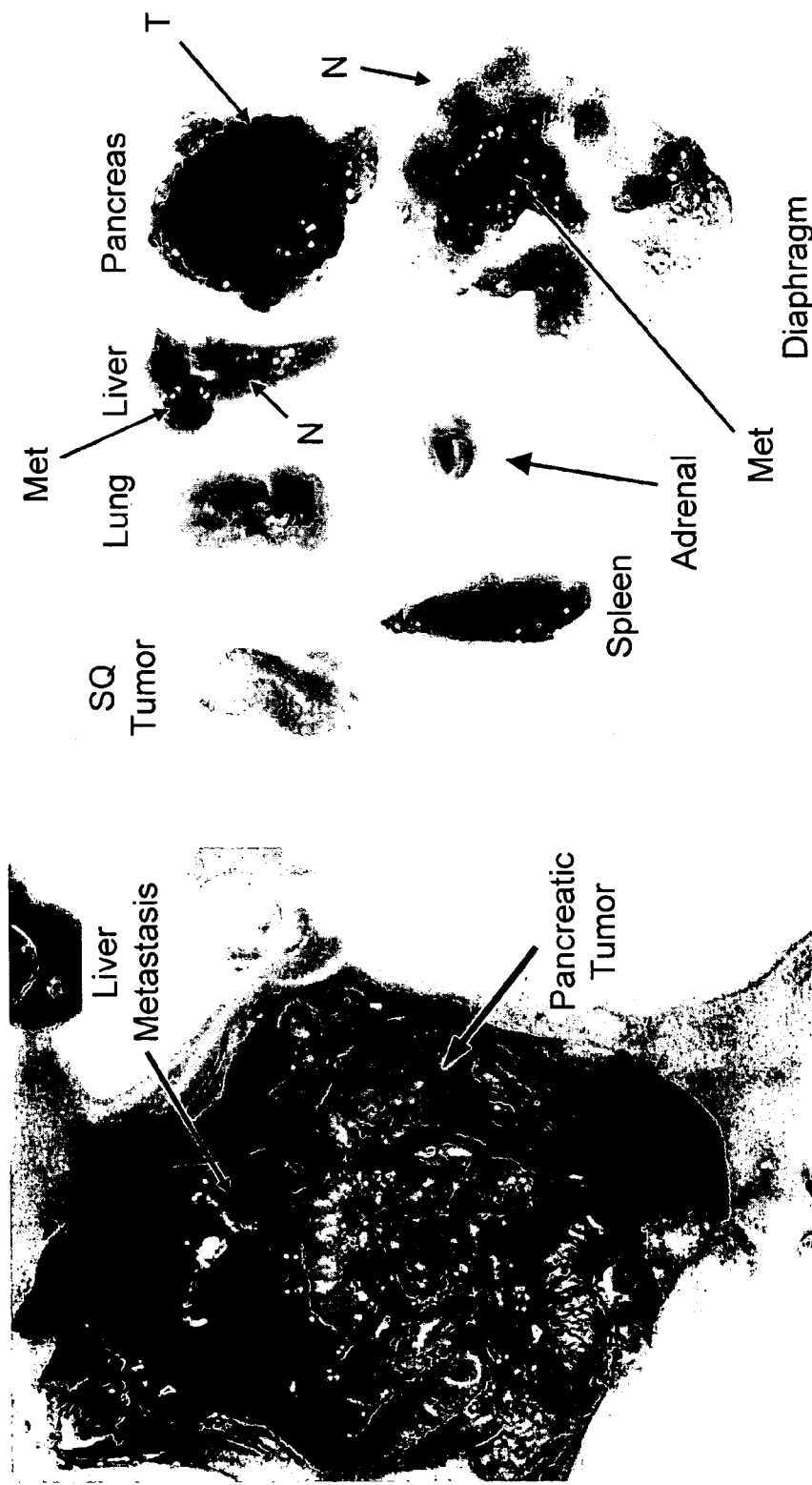

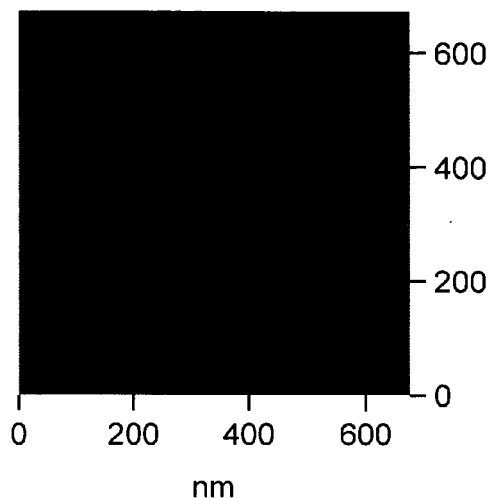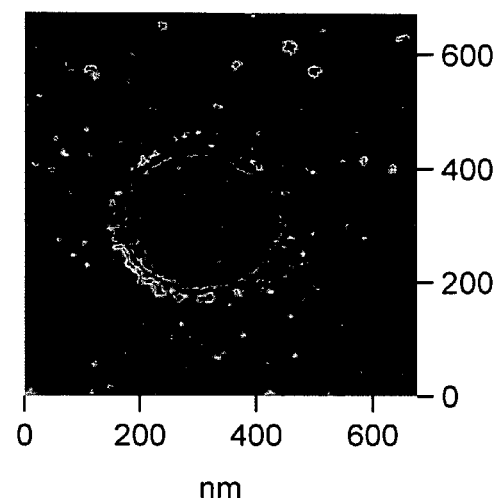
FIG.5A          FIG.5B
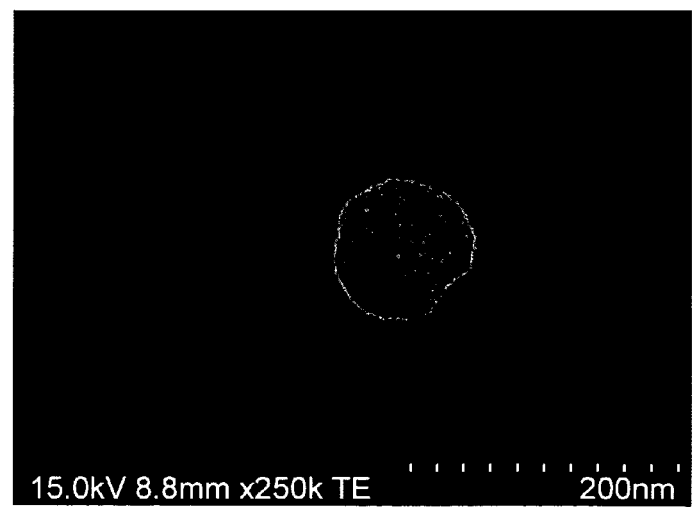
FIG.5C

MR Imaging of DU145 Tumors by Ligand-Liposome Complexes

Baseline

Free Mag scLip-Mag scLip-HK-Mag

Improved MR Imaging of MDA-MB-435 Tumors by 3rd Generation Ligand-Liposome Complex Baseline Free Mag scLip-Mag scLip-HK-Mag Improved MRI Imaging of Pancreatic Tumor and Metastatic Lesions Using 3rd Generation Nanocomplex Including the HK Peptide
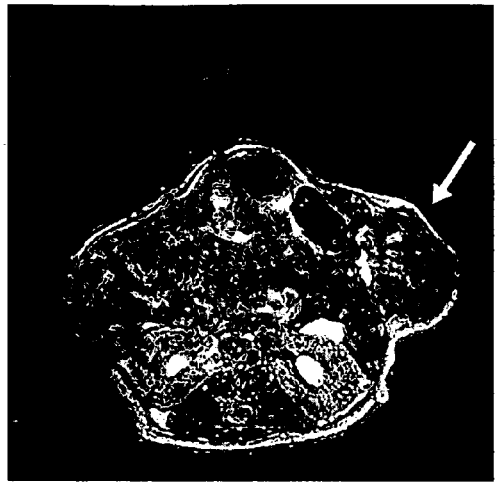
FIG. 9C scL-HK-Mag
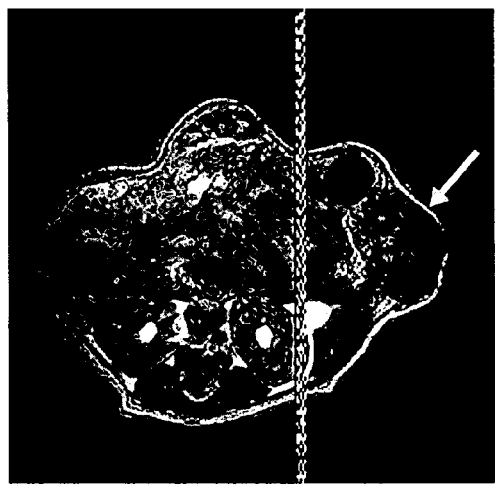
FIG. 9B scLip-Mag
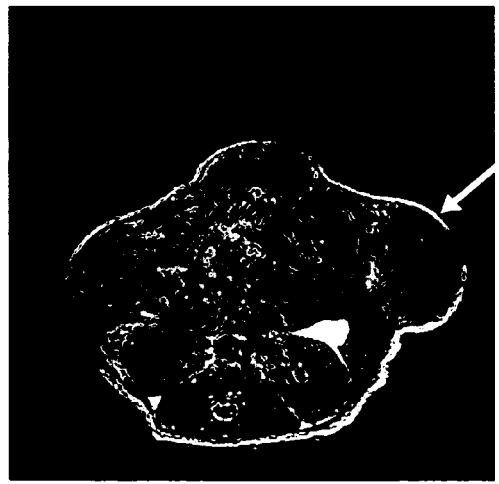
FIG. 9A Baseline MR Imaging of Pancreatic cancer metastasis by systematically delivered Nanocomplex gad-d
FIG. 11A Baseline
FIG. 11B Complex
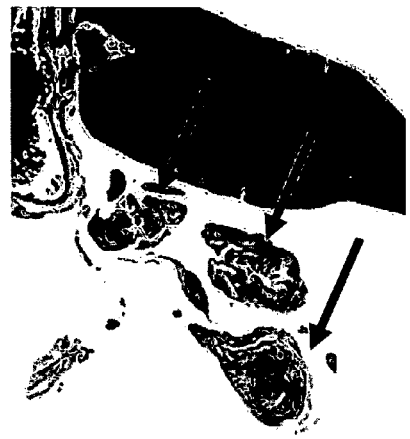
FIG. 11C Greater Enhancement of Metastases on MRI Images with Complex vs Gad-d p<0.04 for six matched nodules
(25 days post-inoculation)

PI = Pixel intensity

Base (PI 5413)

Base (PI 6313)

Complex (PI 10137)

Gad-d (PI)

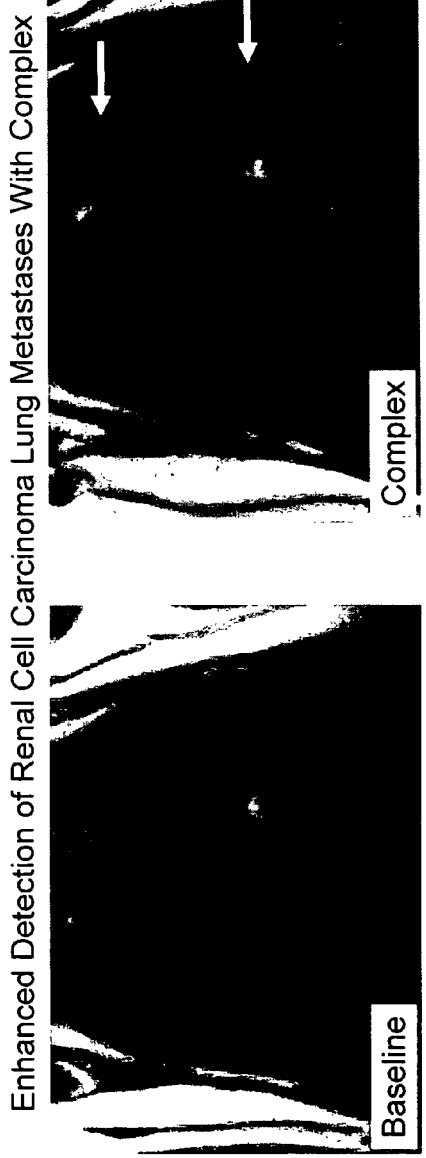
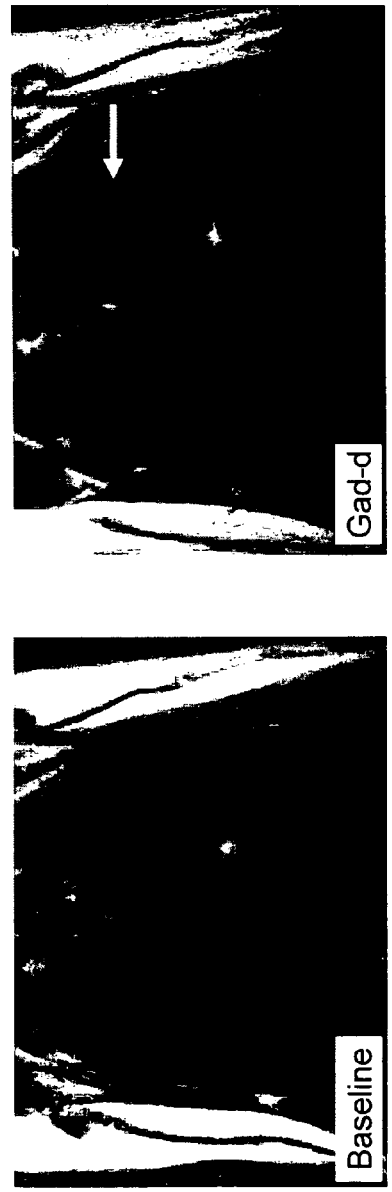
Enhanced Detection of Renal Cell Carcinoma Lung Metastases With Complex
FIG. 13A  Baseline
FIG. 13B  Complex — 4 pixels = approx 0.4 mm
FIG. 13C  Baseline
FIG. 13D  Gad-d — 5 pixels is equivalent to approx 3 mm in human lung CT

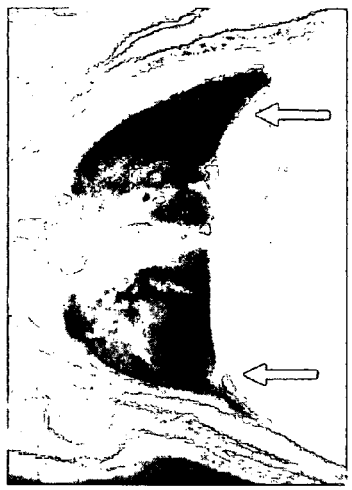
FIG.18C Complex at 2 hr
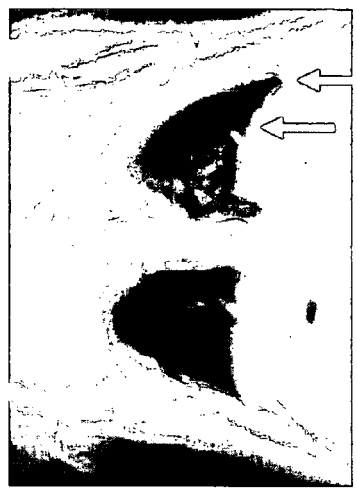
FIG.18F Complex at 2 hr
Renal Cell Carcinoma Sub pleural metastases
Two slices (8 days post-inoculation)
FIG.18B Complex at 1 hr
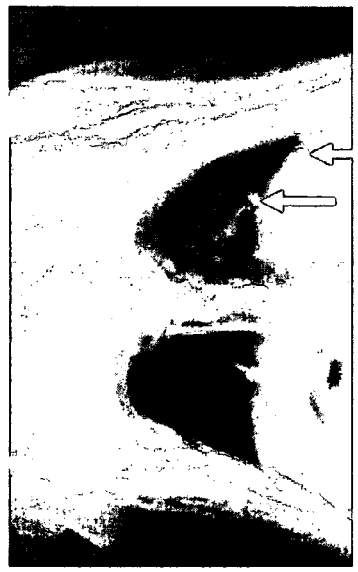
FIG.18E Complex at 1 hr
FIG.18A Base
FIG.18D Base Detection of $B_{16}/F_{10}$ Lung Metastases by TfRscFv-Lip-Mag

TUMOR-TARGETED NANODELIVERY SYSTEMS TO IMPROVE EARLY MRI DETECTION OF CANCER

CROSS REFERENCE TO RELATED APPLICATIONS

The present application is a continuation-in-part of U.S. application Ser. No. 10/113,927, filed Apr. 2, 2002, which is a continuation-in-part of U.S. application Ser. No. 09/914,046, filed Oct. 1, 2001. U.S. application Ser. No. 09/914,046, is a U.S. National Phase Application under 35 U.S.C. §371 of PCT/US00/04392, filed Feb. 22, 2000, which claims the benefit of U.S. Provisional Application No. 60/121,133, filed Feb. 22, 1999. U.S. application Ser. No. 10/113,927 also claims the benefit of U.S. Provisional Application No. 60/280,134, filed Apr. 2, 2001. The present application also claims the benefit of U.S. Provisional Application No. 60/728,303, filed Oct. 20, 2005. The disclosures of each of these applications are incorporated by reference herein in their entireties for all purposes.

BACKGROUND OF THE INVENTION

1. Field of the Invention

The present invention is in the fields of drug delivery, cancer treatment and diagnosis and pharmaceuticals. This invention provides a method of making antibody- or antibody fragment-targeted immunoliposomes for the systemic delivery of molecules to treat and image diseases, including cancerous tumors. The invention also provides immunoliposomes and compositions, as well as methods of imaging various tissues. The liposome complexes are useful for encapsulation of imaging agents, for example, for use in magnetic resonance imaging. The specificity of the delivery system is derived from the targeting antibodies or antibody fragments.

2. Background of the Invention

The ability to detect cancer, both primary and metastatic disease, at an early stage would be a major step towards the goal of ending the pain and suffering from the disease. The development of tumor targeted delivery systems for gene therapy has opened the potential for delivery of imaging agents more effectively than is currently achievable. Magnetic resonance imaging (MRI) can acquire 3-Dimensional anatomical images of organs. Coupling these with paramagnetic images results in the accurate localization of tumors as well as longitudinal and quantitative monitoring of tumor growth and angiogenesis. (Gillies, R. J., et al., *Neoplasia* 2:139-451 (2000); Degani, H., et al., *Thrombosis & Haemostasis* 89:25-33 (2003)).

One of the most common paramagnetic imaging agents employed in cancer diagnostics is Magnevist® (Gadopentetate Dimeglumine) (Mag) (Berlex Imaging, Montville, N.J.). Gadolinum is a rare earth element. It shows paramagnetic properties since its ion ($Gd^{++}$) has seven unpaired electrons. The contrast enhancement observed in MRI scans is due to the strong effect of $Gd^{++}$ primarily on the hydrogen-proton spin-lattice relaxation time (Ti). While free gadolinium is highly toxic, and thus unsuitable for clinical use, chelation with diethylenetriamine pentacetic acid (DTPA) generates a well tolerated, stable, strongly paramagnetic complex. This metal chelate is metabolically inert. However, after i.v. injection of gadopentetate dimeglumine, the meglumine ion dissociates from the hydhophobic gadopentetate, which is distributed only in the extracellular water. It cannot cross an intact blood-brain barrier, and therefore does not accumulate in normal brain tissue, cysts, post-operative scars, etc, and is rapidly excreted in the urine. It has a mean half-life of about 1.6 hours. Approximately 80% of the dose is excreted in the urine within 6 hours.

However, there are significant limitations with current contrast media, including that they are mainly based on perfusion and diffusion labels, and glucose uptake. With these free (non-complexed) agents, changes are seen in tumors, in inflammatory disease, and even with hormonal effects (in breast) (e.g. most gadolinium based and iodine based contrast agents document perfusion and diffusion into interstitial space, FDG-PET demonstrates glucose uptake). Thus, tumors are not specifically targeted by these contrast agents. In addition, active benign processes cannot always be separated from malignant, e.g. benign enhancing areas on breast MRI, chronic pancreatitis vs pancreatic carcinoma. There is also insufficient uptake by small tumors of these agents, and thus poor sensitivity and lack of early detection which is particularly critical in diseases like lung cancer. It may not be possible to detect solitary pulmonary nodules or pleural nodules. What is a needed, therefore, is a mechanism for delivering such agents to specific tissues within the body, for example, to tumor tissues and metastases.

BRIEF SUMMARY OF THE INVENTION

In one embodiment, the present invention provides methods of preparing an antibody- or antibody fragment-targeted cationic immunoliposome complex comprising preparing an antibody or antibody fragment, mixing the antibody or antibody fragment with a cationic liposome to form a cationic immunoliposome, wherein the antibody or antibody fragment is not chemically conjugated to the cationic liposome, and mixing the cationic immunoliposome with an imaging agent to form the antibody- or antibody fragment-targeted-cationic immunoliposome complex. Exemplary antibody fragments for use in the practice of the present invention include, single chain Fv fragments, such as an anti-transferrin receptor single chain Fv (TfRscFv) and anti-HER-2 antibody or antibody fragment. In additional embodiments, the methods further comprise mixing the cationic immunoliposome with a peptide comprising the K[K(H)KKK]5-K(H)KKC (HoKC) (SEQ ID NO: 1) peptide.

Suitably, the antibody or antibody fragment is mixed with said cationic liposome at a ratio in the range of about 1:20 to about 1:40 (w:w). Suitably, the cationic liposomes comprise a mixture of dioleoyltrimethylammonium phosphate with dioleoylphosphatidylethanolamine and/or cholesterol; or a mixture of dimethyldioctadecylammonium bromide with dioleoylphosphatidylethanolamine and/or cholesterol.

In additional embodiments, the cationic immunoliposomes are mixed with the imaging agent at a ratio in the range of about 1:10 to about 1:35 (mg imaging agent:μg liposome), suitably about 1:14 to about 1:28 (mg imaging agent:μg liposome), or about 1:21 (mg imaging agent:μg liposome). Exemplary imaging agents for use in the practice of the present invention include, but are not limited to, magnetic resonance imaging (MRI) agents, such as gadolinium, gadopentetate dimeglumine, iopamidol and iron oxide. Also, barium, iodine and saline imaging agents for CT, $^{18}$F-2-deoxy-2-fluoro-D-glucose (FDG) and other imaging agents for PET can also be used.

The present invention also provides cationic immunoliposome complexes prepared by the methods of the present invention and antibody- or antibody fragment-targeted cationic immunoliposome complexes comprising a cationic liposome, an antibody or antibody fragment, and an imaging agent, wherein the antibody or antibody fragment is not chemically conjugated to said cationic liposome.

In further embodiments, the present invention provides methods of imaging an organ or a tissue, and also for distinguishing between benign tissues/diseases and cancerous tissues/diseases in a patient comprising administering the cationic immunoliposome complexes of the present invention to the patient prior to performing the imaging. Administration can occur via any route, for example, intravenous administration, intramuscular administration, intradermal administration, intraocular administration, intraperitoneal administration, intratumoral administration, intranasal administration, intracereberal administration or subcutaneous administration. Suitably, the tissue that is imaged using the methods and complexes of the present invention are cancerous tissues, including cancerous metastasis.

The present invention also provides methods of imaging and treating a tumor tissue in a patient suffering from cancer comprising administering the cationic immunoliposome complexes of the present invention to the patient to image the tumor tissue and administering an anti-cancer agent to the patient to treat the tumor tissue. Exemplary anti-cancer agents include nucleic acids, genes, proteins, peptides, small molecules, chemotherapeutic agents, such as docetaxel, mitoxantrone and gemcitabine, and antisense oligonucleotides or siRNA.

Additional embodiments of the present invention will be familiar to one of ordinary skill in the art.

BRIEF DESCRIPTION OF THE DRAWINGS/FIGURES

FIGS. 1A and 1B show tumor-specific targeting of a CaPan-1 orthotopic metastasis model by the TfRscFv-Liposome-DNA nanocomplex. The same tumor nodule in the liver indicated by an arrow in 1A exhibits intense β-galactosidase expression in 1B. 1A=gross necropsy; 1A=tissues after staining for β-galactosidase.

FIG. 2A-2C show In Vitro MR Imaging of K564 cells after transfection with the TfRscFv-Lip-Mag nanocomplex. 1A=time dependent transfection. The values given are relative intensity. 1B=shows variation in relative intensity with the amount of Magnevist® included in the complex (in µl). 1C=Comparison of relative intensity of the TfRscFv-Lip-Mag complex versus free Magnevist®. The small circles in all images are markers for sample orientation.

FIG. 3A-I show improved MR imaging in two different models of cancer using the Ligand-Liposome-Mag nanocomplex. 3A, D, and G show the differences in MRI signal in a large pancreatic orthotopic tumor (arrow) (4 months after surgical implantation of the tumor) between the i.v. administered free contrast agent and the TfRscFv-Lip-Mag complex. 3B, E, and H show a similar effect in a second mouse with a subcutaneous pancreatic tumor and a much smaller abdominal pancreatic tumor (arrows). 3C, F and I are the images of a third animal with a subcutaneous prostate tumor (arrow) in which the same effect is evident.

FIG. 4A-C show SPM phase images of liposomes without Magnevist®. The images appearing in 4A, 4B and 4C were obtained at setpoints of 1.68 V, 1.45 V, and 1.35 V, respectively. The corresponding phase differences between the non-compliant substrate and the mechanically compliant liposome are −3.5°, +8°, and +40°. The interaction of the SPM tip and liposome changes from attractive to repulsive as the setpoint is decreased.

FIG. 5A-C show SPM and SEM images of liposome-encapsulated Magnevist® (Lip+Mag). 5A is the Atomic Force Microscopy topographical image of the Liposome encapsulated Magnevist® particle. The SPM phase image (setpoint=1.6) (5B) and 15 keV SEM (TE) [Transmission-mode electron detector] image (5C) possess similar contrast, although generated by entirely distinct complementary physical mechanisms.

FIGS. 6A and 6B show SPM topographic and phase imaging of TfRscFv+Lip+Mag nanocomplex. 6A is the 15 keV SEM (TE) [Transmission-mode electron detector] image of the full nanocomplex. 6B=A lower power image of the field. The boxed area is the image in 6A.

FIGS. 7A and 7B show cross-sectional comparison of SPM topographic and magnetic phase image in lift mode using 25-nm height displacement. 7A is an SPM topographic/magnetic phase image of the full TfRscFv-Lip-Mag nanocomplex. The appearance of a double dipole-like signal in 7B consisting of attractive and repulsive in-plane magnetic interactions suggests that the cause of this interaction is the non-uniform toroidal distribution of Magnevist within the NDS, consistent with SEM and nonmagnetic SPM phase images.

FIGS. 8A-8H show improved MR imaging in two different models of cancer using the Ligand-HK-Liposome-Mag nanocomplex. Human breast cancer MDA-MB-435 (FIG. 8E-8H) and human prostate cancer cell line (DU145) (FIG. 8A-8D).

FIG. 9A-C shows tumor-specific targeting of a CaPan-1 subcutaneous tumor and orthotopic metastasis model by the TfRscFv-HK-Liposome-Mag nanocomplex.

FIG. 11A-11C shows MR imaging of pancreatic cancer metastases by Mag-comprising complexes of the present invention.

FIG. 13A-13D shows a greater enhancement in MR imaging of renal cell carcinoma lung metastases by Mag-comprising complexes of the present invention.

FIG. 15A-15B shows MR imaging of very small metastases by Mag-comprising complexes of the present invention, demonstrating the sensitivity of the complexes of the present invention.

FIG. 18A-18F shows MR imaging of metastases in the subpleura of the lung by Mag-comprising complexes of the present invention.

DETAILED DESCRIPTION OF THE INVENTION

Figure 2A:
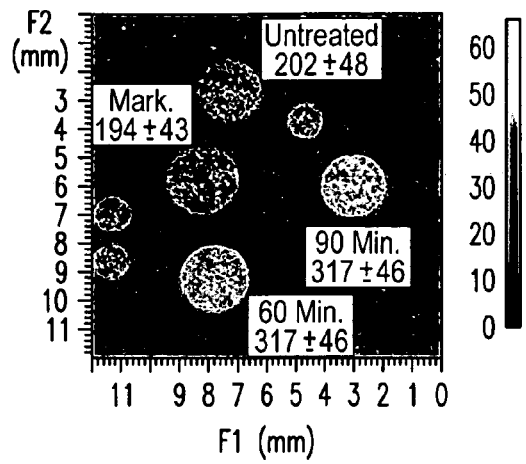

The present invention fulfills a critical need, that is, enhanced sensitivity and tumor-cell specificity for early detection and differential diagnosis of tumor versus benign tissue, by providing nanocomplexes for systemic delivery of imaging agents, such as magnetic resonance imaging (MRI) agents, such as gadolinium, gadopentetate dimeglumine (Magnevist®) and, iopamidol, iron oxide; barium, iodine and saline imaging agents for CT; and $^{18}$F-2-deoxy-2-fluoro-D-glucose (FDG) and other imaging agents for PET to targeted tissues, for example tumors. Scanning Electron Microscopy (SEM) and Scanning Probe Microscopy (SPM) (Wolfert, M. A., et al., *Human Gene Therapy* 7:2123-2133 (1996); Dunlap, D. D., et al., *Nucleic Acids Research* 25:3095-3101 (1997); Kawaura, C., et al., *FEBS Letters* 421:69-72 (1998); Choi, Y. H., et al., *Human Gene Therapy* 10:2657-2665 (1999); Diebel, C. E., et al., *Nature* 406:299-302 (2000); Rasa, M., et al., *J. Coll. Interface Sci* 250:303-315 (2002)) have been used to examine the physical structure and size of these imaging agent-carrying nanocomplexes. In the case of gadolinium, a high-atomic number element which possess a large magnetic moment, these properties can be exploited in a variety of ways to enhance contrast in both SEM and SPM. The findings presented herein demonstrate that the liposome nanocomplexes of the present invention do indeed encapsulate imaging agents, such as Magnevist®, and that intravenous administration of these complexes result in enhanced tumor imaging. The present invention provides the unexpected and surprising results of detection of very small metastases, include pleural metastases in the lung, as well as the ability to differentiate between benign and cancerous tissues.

In one embodiment, the present invention provides tumor-targeting delivery systems comprising contrast agents, for example magnetic resonance imaging (MRI) contrast agents. U.S. Published Patent Application No. 2003/0044407 (the disclosure of which is incorporated herein by reference in its entirety) discloses these nano-sized, cationic liposome encapsulating various agents. Decorating the surface of these liposomes are targeting molecules which can be a ligand, such as folate or transferrin, or an antibody or an antibody fragment directed against a cell surface receptor. The presence of the ligand/antibody on the liposomes facilitates the entry of the complexes into the cells through binding of the targeting molecule by its receptor followed by internalization of the bound complex via receptor mediated endocytosis, a highly efficient internalization pathway (Cristiano, R. J., and Curiel, D. T., *Cancer Gene Therapy* 3:49-57 (1996); Cheng, P. W., *Human Gene Therapy* 7:275-282 (1996)). This modification of the liposomes results in their being able not only to selectively deliver their payload to tumor cells, but also increases the transfection efficacy of the liposome. Transferrin receptor (TfR) levels are elevated in various types of cancer including oral, prostate, breast, and pancreas (Keer, H. N., et al., *Journal of Urology* 143:381-385 (1990); Rossi, M. C., and Zetter, B.R., *Proc. Natl. Acad. Sci. (USA)* 89:6197-6201 (1992); Elliott, R. L., et al., *Ann. N.Y Acad. Sci.* 698: 159-166 (1993); Thorstensen, K., and Romslo, I., *Scand. J. Clin. Lab. Investig.* (Supp.) 215:113-120 (1993); Miyamoto, T., et al., *Int'l. J. Oral Maxillofacial Surg.* 23:430-433 (1994); Ponka, P. and Lok, C. N., *Int'l. J. Biochem. Cell Biol.* 31:1111-1137 (1999)). Moreover, the TfR recycles during internalization in rapidly developing cells such as cancer cells (Ponka, P. and Lok, C. N., *Int'l. J. Biochem. Cell Biol.* 31:1111-1137 (1999)), thus contributing to the uptake of these transferrin targeted nanocomplexes even in cancer cells where TfR levels are not elevated. In suitable embodiments, the nanocomplexes described herein employ an anti-transferrin receptor single chain anti-body fragment (TfRscFv) as the targeting moiety (Haynes, B. F., et al., *J. Immunol.* 127:347-351 (1981); Batra, J. K., et al., *Molecular & Cellular Biology* 11:2200-2205 (1991)). TfRscFv contains the complete antibody binding site for the epitope of the TfR recognized by the monoclonal antibody 5E9 (Batra, J. K., et al., *Molecular & Cellular Biology* 11:2200-2205 (1991)). TfRscFv has advantages over the Tf molecule itself, or an entire Mab, in targeting liposomes to cancer cells with elevated TfR levels: 1) the size of the scFv (28 kDa) is much smaller than the Tf molecule (80 kDa) or the parental Mab (155 kDa). The scFv-liposome-DNA complex may thus exhibit better penetration into small capillaries characteristic of solid tumors. 2) the smaller scFv has a practical advantage related to the scaled-up production necessary for the clinical trials. 3) the scFv is a recombinant molecule and not a blood product like Tf and thus presents no danger of a potential contamination by blood borne pathogens. 4) without the Fc region of the Mab, the issue of non-antigen-specific binding through Fc receptors is eliminated (Jain, R.K. and Baxter, L. T., *Cancer Res.* 48:7022-7032 (1988)). Such an anti-TfR single chain antibody molecule can target an intravenously administered cationic liposome-DNA nanocomplex preferentially to tumors (See U.S. Published Patent Application No. 2003/0044407; Xu, L., et al., *Molecular Medicine* 7:723-734 (2001); Xu L, et al., *Molecular Cancer Therapeutics* 1:337-346 (2002)). Encapsulating Magnevist® (Mag) within such a tumor-targeted nanocomplexes offers advantages for enhanced sensitivity and detection of tumor metastases and diagnosis of cancer. Gadolinium, gadopentetate dimeglumine (Magnevist®), iopamidol, iron oxide; barium, iodine and saline imaging agents for CT; and $^{18}$F-2-deoxy-2-fluoro-D-glucose (FDG) and other imaging agents for PET, as well as any other current contrast agent known to one of ordinary skill in the art, as well as any future contrast agent or imaging agent yet to be developed (e.g., for MRI, CT, PET, SPECT, etc.) can also be encapsulated within the immunoliposomes of the present invention.

Antibody- or antibody fragment-targeted cationic liposome complexes in accordance with this invention are made by a simple and efficient non-chemical conjugation method in which the components of the desired complex are mixed together in a defined ratio and in a defined order (see, U.S. Published Patent Application No. 2003/0044407). The resultant complexes are as effective as, or more effective than, similar complexes in which the antibody or antibody fragment is chemically conjugated to the liposome or polymer. The terms "immunocomplex," "immunoliposome," "complex," "nanocomplex," "immunonanocomplex," "liposome complex" are used interchangeably throughout to refer to the cationic liposomes of the present invention.

Either a whole antibody or an antibody fragment can be used to make the complexes of this invention. In suitable embodiments, an antibody fragment is used. Preferably, the antibody fragment is a single chain Fv fragment of an antibody. One preferred antibody is an anti-TfR monoclonal antibody and a preferred antibody fragment is an scFv based on an anti-TfR monoclonal antibody. A suitable anti-TfR monoclonal antibody is 5E9 (see, e.g., Hayes, B. F., et al., "Characterization of a Monoclonal Antibody (5E9) that Defines a Human Cell Surface Antigen of Cell Activation," *J. Immunol.* 127:347-352 (1981); Batra, J. K., et al., "Single-chain Immunotoxins Directed at the Human Transferring Receptor Containing Pseudomonas Exotoxin A or Diphtheria Toxin: Anti-TFR(Fv)-PE40 and DT388-Anti-TFR(Fv)," *Mol. Cell. Biol.* 11:2200-2205 (1991); the disclosures of which are incorporated herein by reference). An scFv based on 5E9 antibody contains the complete antibody binding site for the epitope of the TfR recognized by this MAb as a single polypeptide chain of approximate molecular weight 26,000. An scFv is formed by connecting the component VH and VL variable domains from the heavy and light chains, respectively, with an appropriately designed linker peptide, which bridges the C-terminus of the first variable region and N-terminus of the second, ordered as either VH-linker-VL or VL-linker-VH. Another preferred antibody is an anti-HER-2 monoclonal antibody, and another preferred antibody fragment is an scFv based on an anti-HER-2 monoclonal antibody.

In suitable embodiments, a cysteine moiety is added to the C-terminus of the scFv. Although not wishing to be bound by theory, it is believed that the cysteine, which provides a free sulfhydryl group, may enhance the formation of the complex between the antibody and the liposome, for example via a charge-charge interaction. With or without the cysteine, the protein can be expressed in E. coli inclusion bodies and then refolded to produce the antibody fragment in active form.

Unless it is desired to use a sterically stabilized immunoliposome in the formation of the complex, a first step in making the complex comprises mixing a cationic liposome or combination of liposomes or small polymer with the antibody or antibody fragment of choice (see Examples herein and in U.S. Published Patent Application No. 2003/0044407). A wide variety of cationic liposomes are useful in the preparation of the complexes of this invention. Published PCT application WO99/25320 describes the preparation of several cationic liposomes. Examples of desirable liposomes include those that comprise a mixture of dioleoyltrimethylammonium phosphate (DOTAP) and dioleoylphosphatidylethanolamine (DOPE) and/or cholesterol (chol), a mixture of dimethyldioctadecylammonium bromide (DDAB) and DOPE and/or chol. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio).

The present invention also provides for targeted-cationic polymers for delivery of imaging agents. Suitable polymers are DNA binding cationic polymers that are capable of mediating DNA compaction and can also mediate endosome release. A preferred polymer is polyethyleneimine. Other useful polymers include polysine, protamine and polyamidoamine dendrimers.

The antibody or antibody fragment is one which will bind to the surface of the target cell, and preferably to a receptor that is differentially expressed on the target cell. The antibody or antibody fragment is mixed with the cationic liposome or polymer at room temperature and at a protein:lipid ratio in the range of about 1:20 to about 1:40 (w:w) or a protein protein polymer ratio in the range of about 0.1:1 to 10:1 (molar ratio).

The antibody or antibody fragment and the liposome or polymer are allowed to incubate at room temperature for a short period of time, typically for about 10-15 minutes, then the mixture is mixed with a therapeutic or diagnostic agent of choice. Examples of therapeutic molecules or agents which can be complexed to the antibody and liposome include genes, high molecular weight DNA (genomic DNA), plasmid DNA, antisense oligonucleotides, peptides, ribozymes, nucleic acids (including siRNA and antisense), viral particles, immunomodulating agents, proteins, small molecules and chemical agents. Preferred therapeutic molecules include genes encoding p53, Rb94 or Apoptin. RB94 is a variant of the retinoblastoma tumor suppressor gene. Apoptin is a gene that induces apoptosis in tumor cells only. In another preferred embodiment, the agent is an antisense oligonucleotide or an siRNA molecule, such as a HER-2 antisense or siRNA molecule. A third type of preferred agent is a diagnostic imaging agent, such as an MRI imaging agent, such as a Gd-DTPA agent. Additional imaging agents include, but are not limited to, Gadolinium, gadopentetate dimeglumine (Magnevist®), iopamidol, iron oxide; barium, iodine and saline imaging agents for CT; and 18F-2-deoxy-2-fluoro-D-glucose (FDG) and other imaging agents for PET. If the agent is DNA, such as the coding region of p53, it can be positioned under the control of a strong constitutive promoter, such as an RSV or a CMV promoter.

The antibody or antibody fragment and liposome combination is mixed with the therapeutic or diagnostic agent at a ratio in the range of about 1:10 to 1:20 (µg of agent:nmole of total lipid) or 1:10 to 1:40 (µg of agent:nmole of total polymer) and incubated at room temperature for a short period of time, typically about 10 to 15 minutes. The size of the liposome complex is typically within the range of about 50-400 nm as measured by dynamic light scattering using a Malvern ZETASIZER® 3000 particle sizer.

In one embodiment of this invention, the liposome used to form the complex is a sterically stabilized liposome. Sterically stabilized liposomes are liposomes into which a hydrophilic polymer, such as PEG, poly(2-ethylacrylic acid), or poly(n-isopropylacrylamide (PNIPAM) have been integrated. Such modified liposomes can be particularly useful when complexed with therapeutic or diagnostic agents, as they typically are not cleared from the blood stream by the reticuloendothelial system as quickly as are comparable liposomes that have not been so modified. To make a sterically stabilized liposome complex of the present invention, the order of mixing the antibody or antibody fragment, the liposome and the therapeutic or diagnostic agent is reversed from the order set forth above. In a first step, a cationic liposome is first mixed with a therapeutic or diagnostic agent as described above at a ratio in the range of about 1:10 to 1:20 (µg of agent:nmole of lipid). To this lipoplex is added a solution of a PEG polymer in a physiologically acceptable buffer and the resultant solution is incubated at room temperature for a time sufficient to allow the polymer to integrate into the liposome complex. The antibody or antibody fragment then is mixed with the stabilized liposome complex at room temperature and at a protein:lipid ratio in the range of about 1:5 to about 1:30 (w:w).

The liposomal or polymer complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a human patient to be benefited by administration of the therapeutic or diagnostic molecule of the complex. The complexes are sized appropriately so that they are distributed throughout the body following i.v. administration. Alternatively, the complexes can be delivered via other routes of administration, such as intratumoral (IT), intralesional (IL), aerosal, percutaneous, endoscopic, topical, intramuscular (IM), intradermal (ID), intraocular (IO), intraperitoneal (IP), intranasal (IN), intracerebereal (IC) or subcutaneous administration. Preparation of formulations for delivery via such methods, and delivery using such methods, are well known in the art.

In one embodiment, compositions comprising the antibody- or antibody fragment-targeted liposome (or polymer) and therapeutic agent complexes are administered to effect human gene therapy. The therapeutic agent component of the complex comprises a therapeutic gene under the control of an appropriate regulatory sequence. Gene therapy for various forms of human cancers can be accomplished by the systemic delivery of antibody or antibody fragment-targeted liposome or polymer complexes which contain a nucleic acid encoding wt p53 or RB94. The complexes can specifically target and sensitize tumor cells, both primary and metastatic tumors, to radiation and/or chemotherapy both in vitro and in vivo.

The complexes can be optimized for target cell type through the choice and ratio of lipids, the ratio of antibody or antibody fragment to liposome, the ratio of antibody or antibody fragment and liposome to the therapeutic or diagnostic agent, and the choice of antibody or antibody fragment and therapeutic or diagnostic agent.

In one embodiment, the target cells are cancer cells. Although any tissue having malignant cell growth can be a target, head and neck, breast, prostate, pancreatic, brain, including glioblastoma, cervical, lung, liver, liposarcoma, rhabdomyosarcoma, choriocarcinoma, melanoma, retinoblastoma, ovarian, urogenital, gastric and colorectal cancers are suitable targets.

The complexes made by the method of this invention also can be used to target non-tumor cells for delivery of a therapeutic molecule or any nucleic acid. While any normal cell can be a target, preferred cells are dendritic cells, endothelial cells of the blood vessels, lung cells, breast cells, bone marrow cells, thymus cells and liver cells. Undesirable, but benign, cells can be targeted, such as benign prostatic hyperplasia cells, over-active thyroid cells, lipoma cells, and cells relating to autoimmune diseases, such as B cells that produce antibodies involved in arthritis, lupus, myasthenia gravis, squamous metaplasia, macular degeneration, cardiovascular disease, neurologic disease such as Alzheimer's disease, dysplasia and the like.

The complexes can be administered in combination with another therapeutic treatment, such as either a radiation treatment or chemotherapeutic agent. The therapeutic treatments, or a combination of therapeutic treatments, can be administered before or subsequent to the administration of the complex, for example within about 12 hours to about 7 days. Chemotherapeutic agents include, for example, doxorubicin, 5-fluorouracil (5FU), cisplatin (CDDP), docetaxel (TAXOTERE®), gemcitabine (GEMZAR®), pacletaxel, vinblastine, etoposide (VP-16), camptothecia, actinomycin-D, mitoxantrone and mitomycin C. Radiation therapies/treatments include gamma radiation ($^{137}$Cs), X-rays, UV irradiation, microwaves, electronic emissions and the like. Additional therapeutic agents include small molecules, peptides, proteins and the like.

Diagnostic or imaging agents also can be delivered to targeted cells via the liposome or polymer complexes. The terms "diagnostic agents" and "imaging agents" are used interchangeably throughout to refer to agents which can be detected, visualized, imaged or observed in vivo following administration. Exemplary methods for detecting, visualizing, imaging or observing diagnostic and imaging agents are well known in the art and include, for example, optical imaging such as fluorescent imaging (fluorimeters) or bioluminescent imaging, positron emission tomography (PET) scanning, single photon emission computed tomography (SPECT) scanning, magnetic resonance imaging (MRI), x-ray, radionucleotide imaging (e.g., gamma camera, computed tomography (CT), quantitative autoradiography, etc.) and the like. Exemplary diagnostic agents include electron dense materials, iron, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. MRI agents such as a Gd-DTPA agent, gadolinium, or Magnevist® (Gadopentetate Dimeglumine) (Mag) (Berlex Imaging, Montville, N.J.). Imaging agents disclosed by Low et al. in U.S. Pat. No. 5,688,488, incorporated herein by reference, are useful in the present invention. Additional imaging agents include, but are not limited to, iopamidol (e.g., ISOVUE®, Regional Health Limited, Aukland, AU), iron oxide; barium, iodine and saline imaging agents for CT; and $^{18}$F-2-deoxy-2-fluoro-D-glucose (FDG) and other imaging agents for PET.

The complexes made in accordance with the method of this invention can be provided in the form of kits for use in the systemic delivery of a therapeutic or diagnostic molecule by the complex. Suitable kits can comprise, in separate, suitable containers (or in a single container), the liposome, the antibody or antibody fragment, and the therapeutic or diagnostic agent. The components can be mixed under sterile conditions in the appropriate order and administered to a patient within a reasonable period of time, generally from about 30 minutes to about 24 hours, after preparation. The kit components preferably are provided as solutions or as dried powders. Components provided in solution form preferably are formulated in sterile water-for-injection, along with appropriate buffers, osmolarity control agents, etc.

Encapsulation and Delivery of Imaging Agents

In certain embodiments, the present invention provides cationic liposomal complexes wherein one or more imaging agents are encapsulated within the interior of the liposome, contained within the hydrocarbon chain region of the bilayer, complexed/associated with the inner and/or outer monolayer (e.g., via static interaction or chemical/covalent interaction), or a combination of any or all of these possibilities. Suitably, the imaging agents will be encapsulated within the interior of the liposome and/or associated with an inner and/or outer monolayer.

As used herein, the terms "diagnostic agents" and "imaging agents" refer to agents which can be detected, visualized, imaged or observed in vivo following administration. Exemplary imaging agents include electron dense materials, iron, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. MRI agents such as a gadolinium, Gd-DTPA agent, or Magnevist® (Gadopentetate Dimeglumine) (Mag) (Berlex Imaging, Montville, N.J.). Imaging agents disclosed by Low et al. in U.S. Pat. No. 5,688,488, incorporated herein by reference, are also useful in the present invention. Additional imaging agents include, but are not limited to, iopamidol (e.g., ISOVUE®, Regional Health Limited, Aukland, AU), iron oxide; barium, iodine and saline imaging agents for CT; and $^{18}$F-2-deoxy-2-fluoro-D-glucose (FDG) and other imaging agents for PET.

As described herein, imaging agents are suitably encapsulated, contained or complexed/associated with the liposome complexes of the present invention by simply mixing the one or more imaging agents with the liposomes during processing. Suitable ratios of imaging agents:liposome complexes are readily determined by the ordinarily skilled artisan. For example, the ratio of imaging agents to liposome complex is suitably in the range of about 1:10 to about 1:35 (mg imaging agent:µg liposome), more suitably about 1:14 to about 1:28 (mg imaging agent:µg liposome), or about 1:21 (mg imaging agent:µg liposome).

As described throughout, examples of desirable cationic liposomes for delivery/encapsulation of imaging agents include those that comprise a mixture of dioleoyltrimethylammonium phosphate (DOTAP) and dioleoylphosphatidylethanolamine (DOPE) and/or cholesterol (chol); and a mixture of dimethyldioctadecylammonium bromide (DDAB) and DOPE and/or chol. The ratio of the lipids can be varied to optimize the efficiency of uptake of the imaging agents. The liposome can comprise a mixture of one or more cationic lipids and one or more neutral or helper lipids. A desirable ratio of cationic lipid(s) to neutral or helper lipid(s) is about 1:(0.5-3), preferably about 1:(1-2) (molar ratio). Examples of ratios of various lipids useful in the practice of the present invention include, but are not limited to:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol).

In one embodiment, the present invention provides methods of preparing imaging agent-comprising antibody- or antibody fragment-targeted cationic immunoliposome complexes comprising preparing an antibody or antibody fragment; mixing the antibody or antibody fragment with a cationic liposome to form a cationic immunoliposome, wherein the antibody or antibody fragment is not chemically conjugated to the cationic liposome; and mixing the cationic immunoliposome with one or more imaging agents to form the antibody- or antibody fragment-targeted-cationic immunohposome complex.

In suitable embodiments, the antibody fragment is a single chain Fv fragment, for example, an anti-transferrin receptor single chain Fv (TfRscFv) or an anti-HER-2 antibody or antibody fragment. Examples of suitable lipids for use in preparing the imaging agent-comprising cationic immunoliposomes are described herein, and include, mixtures of dioleoyltrimethylammonium phosphate with dioleoylphosphatidylethanolamine and/or cholesterol; and mixtures of dimethyldioctadecylammonium bromide with dioleoylphosphatidylethanolamine and/or cholesterol. Suitably the antibody or antibody fragment is mixed with the cationic liposome at a ratio in the range of about 1:20 to about 1:40 (w:w) to form a cationic immunoliposome. Suitably, the cationic immunoliposome is mixed with the imaging agent in the range of about 1:10 to about 1:35 (mg imaging agent:µg liposome), more suitably about 1:14 to about 1:28 (mg imaging agent:µg liposome), or about 1:21 (mg imaging agent:µg liposome).

Exemplary imaging agents include those described herein and known in the art. Suitably, the imaging agent is an MRI imaging agent, such as gadolinium, gadopentetate dimeglumine, iopamidol (e.g., ISOVUE®, Regional Health Limited, Aukland, AU), or iron oxide; barium, iodine and saline imaging agents for CT; and $^{18}F$-2-deoxy-2-fluoro-D-glucose (FDG) and other imaging agents for PET.

In additional embodiments, the methods and immunoliposome complexes of the present invention further comprise mixing the cationic immunoliposome with a peptide comprising the K[K(H)KKK]5-K(H)KKC (HoKC or HK) (SEQ ID NO: 1) peptide. The HoKC peptide carries a terminal cysteine to permit conjugation to a maleimide group. Thus, when the HoKC peptide is used, the liposome formulations also suitable include N-maleimide-phenylbutyrate-DOPE (MPB-DOPE) at 0.1 to 50 molar percent of total lipid, more preferably 1-10 molar percent of total lipid, most preferably 5 molar percent of total lipid. The HoKC liposomes are prepared as previously described (Yu, W. et al. Enhanced transfection efficiency of a systemically delivered tumor-targeting immunolipoplex by inclusion of a pH-sensitive histidylated oligolysine peptide, Nucleic Acids Research 32, e48 (2004)).

In a further embodiment, the present invention provides antibody- or antibody fragment-targeted cationic immunoliposome complexes comprising a cationic liposome, an antibody or antibody fragment, and one or more imaging agents, wherein the antibody or antibody fragment is not chemically conjugated to the cationic liposome. The antibody or antibody fragment is suitably associated with the liposome via an interaction (e.g., electrostatic, van der Walls, or other non-chemically conjugated interaction) between the antibody or antibody fragment and the liposome, suitably between a cystein residue on the antibody or antibody fragment and the liposome surface. In general, a linker or spacer molecule (e.g., a polymer or other molecule) is not used to attach the antibodies and the liposome. The imaging agent(s) can be encapsulated within the cationic liposome, contained with a hydrocarbon chain region of the cationic liposome, associated with an inner or outer monolayer of the cationic liposome, or any combination thereof. Suitably, the cationic immunoliposomes of the present invention are unilamellar liposomes (i.e. a single bilayer), though multilamellar liposomes which comprise several concentric bilayers can also be used. Single bilayer cationic immunoliposomes of the present invention comprise an interior aqueous volume in which agents (e.g., imaging agents) can be encapsulated. They also comprise a single bilayer which has a hydrocarbon chain region (i.e., the lipid chain region of the lipids) in which agents (e.g., imaging agents) can be contained. In addition, agents (e.g., imaging agents) can be complexed or associated with either, or both, the inner monolayer and/or the outer monolayer of the liposome membrane (i.e., the headgroup region of the lipids), e.g., via a charge-charge interaction between the negatively charged imaging agents and the positively charged cationic liposomes. In further embodiments, agents (e.g., imaging agents) can be encapsulated/associated/complexed in any or all of these regions of the cationic immunoliposome complexes of the present invention.

In a still further embodiment, the present invention provides methods of imaging an organ or a tissue in a patient comprising administering the imaging agent-comprising cationic immunoliposome complexes of the present invention to the patient prior to performing the imaging. The immunoliposome complexes can be administered via any desired route, including, but not limited to, intravenous (IV), oral, topical, via inhalation, intramuscular (IM) injection, intratumoral (IT) injection, intradermal (ID) injection, intraperitoneal (IP) injection, intranasal (IN) injection, intraocular (IO) injection, intracranial (IC) injection, or other routes. As used herein, the term patient includes both animal patients (e.g., non-human mammals such as dogs, cats, pigs, sheep, etc,) as well as humans. Methods for imaging tissues of patients are well known in the art and include, but are not limited to, PET scanning, SPECT scanning, MRI imaging and the like. Any tissue or organ in a patient can be imaged using the methods and complexes of the present invention. Simply by modifying the targeting ligand on the liposomes, any over-expressed protein or molecule can be targeted.

Suitably, the methods of the present invention are used to image a cancerous tissue in a patient suffering from, or predisposed to, cancer. Cancerous tissues that can be imaged using the methods of the present invention include solid tumors, as well as metastasic lesions. The methods of the present invention can also distinguish cancerous tissues from non-cancerous (benign) tissues.

In further embodiments the present invention provides methods of imaging and treating a tumor tissue in a patient suffering from, or predisposed to, cancer comprising administering the imaging-agent comprising immunoliposome complexes of the present invention to image the tumor tissue, and administering an anti-cancer agent to the patient to treat the tumor tissue.

Examples of anti-cancer agents that can be administered include, but are not limited to small molecules, proteins, peptides, and chemotherapeutic agents such as those described herein, genes, antisense oligonuclotides and siRNA. Exemplary chemotherapeutic agents include, but are not limited to, doxorubicin, 5-fluorouracil (5FU), cisplatin (CDDP), docetaxel (TAXOTERE®), gemcitabine (GEMZAR®), pacletaxel, vinblastine, etoposide (VP-16), camptothecin, actinomycin-D, mitoxantrone and mitomycin C, and an antibody therapy, such as a monoclonal antibody, e.g., HERCEPTIN® (Genentech, San Francisco Calif.). Examples of antisense oligonucloetides and siRNA molecules for use in the practice of the present invention include, but are not limited to, those disclosed in U.S. Published Patent Application No. 2003/0044407 and U.S. patent application Ser. No. 11/520,796, filed Sep. 14, 2006, the disclosures of each of which are incorporated herein by reference in their entireties. Additional anti-cancer agents include peptides, proteins and small molecules (see, e.g., U.S. Provisional Patent Application Nos. 60/800,163, filed May 15, 2006 and 60/844,352, filed Sep. 14, 2006, the disclosures of each of which are incorporated herein by reference in their entireties). The anti-cancer agent (e.g., the chemotherapeutic agent, small molecule, gene or the antisense or siRNA, etc.) can be associated with the cationic immunoliposome that also comprises the imaging agent, or it can be delivered separately, either in a different immunoliposome in accordance with the present invention, or via another carrier or delivery system (for example, IV injection of a chemotherapeutic per normal clinical standards).

In suitable embodiments, the methods of the present invention comprise administering an immunoliposome complex comprising an imaging agent (e.g., MRI imaging agent such as gadopentetate dimeglumine), and an anti-tumor agent at different times (i.e., the complex and the agent can be given at the same time or at different times). Suitably, the anti-cancer agent is administered either before or after the imaging agent-comprising immunoliposome complex, (e.g., at least 1 hour before or after, at least 6 hours before or after, at least 12 hours before or after, at least 24 hours before or after, at least 48 hours before or after, etc., administration of the cationic immunoliposome complex). In still further embodiments, the methods of imaging and treating a tumor tissue in a patient suffering from cancer can further comprise administering radiation treatment to the patient.

Appropriate dosages of the anti-cancer agents (e.g., chemotherapy, genes, small molecules, proteins, peptides, antisense oligonucleotides or siRNA, etc.) and timing for administration in humans are easily determined by those of skill in the art, based on information contained herein and that is readily available in the art. Furthermore, such amounts can be estimated by extrapolating from experiments performed on animals, e.g., mouse, rat, dog or other studies.

Exemplary benefits of utilizing the nanoimmunolipoosme complexes of the present invention (scL and scL-HoKC) to encapsulate and delivery imaging agents include higher concentration in cancer tissues due to the tumor targeting nature of the complexes. As the complex accumulates in cancer cells, there is differentiation of vascular flow and diffusion into interstitial space (as seen with the non-complexed free imaging agents as currently in use in the clinic) from cancer specific imaging. There is also differential enhancement of cancer vs benign processes. Longer vascular and tissue half life permits delayed imaging using the complexes of the present invention. The complexes and methods can be used to image tissues of interest at various depths.

Thus, the methods and complexes of the present invention result not only in enhanced signal in the tumor, but also greater definition of the internal structure of the tumors. More significantly, smaller tumors can be detected leading to earlier detection and thus improved response/survival. These complexes can also be used to distinguish benign from malignant nodules. This helps to accelerate the decision on when to begin treatment. Currently, this is delayed to determine if the nodule increases since it is not certain if is malignant or not. However, since the complexes of this invention preferentially and specifically transfect tumor cells, this would also serve as a confirmation of malignancy, for example if the small nodules seen on lung CT are small malignancies or not. These last two points are of particular significance in lung and pancreatic cancer.

Exemplary types of cancer imaging problems addressed by use of the imaging agent-comprising complexes of the present invention include, in pancreatic cancer, early detection and differentiation from chronic pancreatitis; early detection of metastatic disease to lungs; classification of solitary pulmonary nodules as benign or malignant; classification of small focal areas of increased MR enhancement in breast as benign or malignant.

The complexes of the present invention can also be used to confirm that, using this delivery system, therapeutic genes will likely enter patient specific cancer cells. That is, the fact that the imaging agent-comprising complexes are able to enter cells provides an indication that delivery of therapeutic genes or other agents associated with the complexes of the present invention will also enter these specific cancer cells.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Immunoliposome Complexes Comprising Magnevist®
Materials and Methods
Cell lines

Human lymphoblastic leukemia cell line K562 was obtained from the Lombardi Comprehensive Cancer Center Tissue Culture core facility. These suspension cells were maintained in RPMI1640 supplemented with 10% Heat Inactivated FBS plus 2 mM L-Glutamine, and 50 µg/ml each of penicillin, streptomycion and neomycin. Human pancreatic cancer cell line CaPan-1 (obtained from the American Type Culture Collection (ATCC), 10801 University Boulevard, Manassas, Va. 20110-2209) was derived from a metastatic adenocarcinoma of the pancreas. It was maintained in Iscov's Modified Dulbecco's Medium containing 4 mM L-Glutamine and Sodium Bicarbonate, supplemental with 20% non-Heat Inactivated FBS, 2 mM L-Glutamine and 50 µg/mL each of penicillin, streptomycin and neomycin. Human prostate cancer cell line DU145 (ATCC, Manassas, Va.) was originally derived from a lesion in the brain of a patient with widespread metastatic carcinoma of the prostate. It was maintained in Minimum Essential Medium with Earle's salts (EMEM) supplemented with 10% heat inactivated FBS plus L-glutamine and antibodies as above.

Nanocomplex Formation

Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). When delivering plasmid DNA, the full complex was formed in a manner identical to that previously described (see U.S. Published Patent Application No. 2003/0044407). To encapsulate the imaging agent for in vitro use, the TfRscFv was mixed with the liposome at a specific ratio and incubated at room temperature for 10 minutes. Magnevist® was added to this solution, mixed and again incubated at room temperature for 10 minutes. When stored at 2-8° C. the complex is stable for at least 8 days, as determined by size measurements using a Malvern ZETASIZER® 3000H particle sizer. The cumulants (Z average) average of measurements over this time frame is 112.3±4.67 (S.E.) while the polydispersity (representing the reproducibility of the values during repeat scans) is 0.445±0.03. A range of acceptable sizes for the nanocomplexes is from about 20 to 1000 nm, suitably about 50 to 700 nm and more suitably about 100 to 500 nm. For in vitro transfection, 2 ml of serum-free media was added to the complex prior to transfection. For in vivo use the complex is formed at a ratio of 1 mg imaging agent to 0.33-1.17 µg TfRscFv to 10-35 µg Liposome (suitably 1 mg imaging agent to 0.5 to 1.0 µg TfRScFv to 14-28 µg Liposome, most suitably 1 mg imaging agent to 0.71 µg TfRscFv to 21 µg Liposome) using the above procedure. When prepared for in vivo use, dextrose was added to a final concentration of 5%.

In Vitro Transfection

To transfect suspension cells K562, $15 \times 10^6$ cells in a total volume of 4.0 ml of medium with all supplements except serum (serum free medium) were placed into a 100 mm2 tissue culture dish. Two ml of the transfection solution from above, containing varying amounts of Magnevist®, was added to the cell suspension. The plate was incubated at 37° C. with gentle rocking for the length of time given in the Results section (up to 90 min), after which the cells were gently pelleted (600×g for 7 minutes) at 4° C. in 0.5 ml microcentrifuge tubes and washed three times with 10 ml of serum free medium to remove any excess transfection solution and placed on wet ice until imaged.

In Vivo Tumor Targeting

To assess the tumor selective targeting of the TfRscFv-Lip nanocomplex to primary and metastatic tumors, an orthotopic metastases model using human pancreatic cancer cell line CaPan-1 was used. Subcutaneous xenograft tumors of CaPan-1 were induced in female athymic nude mice by injection of $1 \times 10^7$ CaPan-1 cells suspended in Matrigel™ collagen basement membrane matrix (BD Biosciences). Approximately eight weeks later the tumors were harvested and a single cell suspension of the tumor was prepared. 1.2-$1.5 \times 10^7$ cells, also suspended in Matrigel™ were injected into the surgically exposed pancreas of female athymic nude mice. Five weeks post-surgery, the complex carrying the LacZ gene was i.v. injected 3× over 24 hrs (at 40 µg DNA/injection). 60 hrs later the animals were sacrificed and examined for the presence of metastases and organs stained for β-galactosidase expression using a previously described procedure (Xu, L., et al., *Human Gene Therapy* 10:2941-2952 (1999)).

MRI Imaging

For in vitro MRI imaging, the cell pellets in microcentrifuge tubes were positioned at the center of the magnet. The MR imaging was performed at Howard University using a 4.7T horizontal bore NMR machine (Varian Inc, Palo Alto, Calif.). The imaging protocols consist of a multi-slice T1-weighted spin echo imaging sequence and a saturation-recovery sequence. For the T1-weighted imaging technique, the repetition time (TR) was 1000 ms, and the echo time (TE) was 13 ms. The T1-weighted spin-echo imaging technique was applied to verify the positive image enhancement. The saturation-recovery MR sequence with variable echo times was used for the T1 measurement. The slice thickness of images was 0.5mm. The RF coil employed was a 30 mm single loop coil. The RF coil serves as an RF transmitter and receiver. The RF pulse was a selective 5 ms sinc pulse. The number of phase encoding steps was 256. The field-of-view was 15 mm×15 mm. The image area chosen in the study was located at the center of the RF coil for RF homogeneity. The MR images were taken in the cross-section direction of the microcentrifuge tube. The height of the cell pellet was 12 mm. The range of the multi-slice images covers the whole pellet. The center slice images, which were not influenced by the image distortion due to the susceptibility effect from the air-pellet boundary, were utilized for the studies. The image intensity was measured using the Varian Image Browser software. The signal is taken from a region-of-interest, which is big enough to cover two thirds of the image from each microcentrifuge tube. The relative image intensities of the pellets from these tubes were applied for contrast enhancement evaluation and the T1 measurements.

For the in vivo studies, mice bearing CaPan1 orthotopic tumors or DU145 subcutaneous xenograft tumors were employed. The CaPan-1 tumors were induced as described above. DU145 tumors were induced by the subcutaneous inoculation of $7 \times 10^6$ cells in Matrigel. These studies were performed at Georgetown University. Animals to be imaged were anesthetized and placed in a proprietary, in-house designed, animal management system. This system incorporates a warm water heating system that maintains the temperature at 37° C., as well as a four channel thermal optical monitoring system used to monitor animal's skin temperature, ambient temperature and wall temperature of the device. For imaging, anesthesia was induced using isoflurane at 4%, with the remaining gas comprised of a 66% oxygen and 30% nitrous oxide mixture. Maintenance of anesthesia was achieved with 1.5% isoflurane under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted Turbo RARE (rapid acquisition with rapid enhancement) three-dimensional imaging sequences performed on a 7T Bruker BioSpin (Germany/USA) imaging console. The imaging parameters used were: T1-weighted Turbo-RARE 3D (3-dimensional), TE 13.3 ms, TR 229.5, Flipback on, 4 echoes with a field of view of 8.0/3.5/3.5 cm and a 256×256×256 matrix. After a baseline image was acquired, the animal was kept immobilized in the animal holder and the Magnevist® only (diluted to 400 µl with 1× Phosphate Buffered Saline pH=7.4) or the Magnevist®-comprising immunoliposome complex (TfRscFv-Lip-Mag) (total volume 400 µl) was systemically administered using a 27G needle by intravenous injection into the tail vein of the animal and the 3-D imaging sequence was immediately initiated. The imaging with the two solutions were performed on sequential days.

Scanning Electron Microscopy (SEM)

Sample solutions of liposome-encapsulated Magnevist® contrast agent, and complete nanocomplex consisting of a tumor-targeting single-chain transferrin receptor protein coating the liposome-encapsulated complex, TfRscFv-Lip-Mag, were prepared at GUMC, delivered to NIST and were stored under dark and refrigeration. For each imaging session, a fresh dilution 1:3 by volume with deionized water was prepared and a 5 µL droplet was micropipetted onto a standard 200-mesh TEM grid consisting of 30-60 nm formvar and 15-20 nm carbon. The droplet was allowed to dry on the grid in air for 5 minutes before loading into the vacuum chamber of the microscope. Imaging was performed using an Hitachi S-4800 field-emission microscope at NIST. Of particular interest to applications of SEM to NDA imaging is a comparison of upper and lower secondary electron detectors [SE(U) and SE(L)]—using the SEM in its usual mode—to the addition of a transmitted electron (TE) detector, transforming the instrument into a low voltage STEM.

Scanning Probe Microscopy (SPM)

Samples solutions of liposome-encapsulated Magnevist® contrast agent, and complete nanocomplex were prepared at GUMC, delivered to NIST and were stored under dark and refrigeration. For each imaging session, a fresh dilution 1:3 by volume with deionized water was prepared and a 5 µl droplet was micropipetted onto an untrasonically cleaned silicon substrate used with native oxide or with a poly-L lysine coating. SPM imaging were obtained using a Veeco MultiMode microscope with a NANOSCOPE® IV microscope controller. Topography by tapping mode with Z control (Veeco RTESP cantilevers for .about.320-360 kHz and k .about.20-60 N/m), phase imaging, and magnetic force microscopy using magnetic coated tips (Veeco MESP 68 kHz) were performed in life mode. Dynamic imaging of dewetting and surface energy "phase separation" as the solution evaporates to expose isolated nanoparticles and aggregates were used to understand the consequences of solvent drying on the stability of the particles and its effect on the various SPM contrast mechanisms available with the SPM system.

Results

Tumor Specific Targeting by the Ligand-Liposome Nanocomplex Carrying a Reporter Gene To assess selective targeting of the TfRscFv-LipA nanocomplex to primary tumor and metastases an orthotopic metastasis model, a closer approximation of the clinical situation, using human PanCa cell line CaPan-1 was employed. Surgical orthotopic implantations of CaPan-1 xenograft tumor sections into nude mice have been shown to produce within 56 days, metastases in liver and spleen (Alisauskus,R., et al., *Cancer Research* 55:5743s-5748s (1995)). Orthotopic tumors of CaPan-1 were induced in female athymic nude mice as described in Methods. Approximately 5 weeks later, the animals were euthanized and necropsied to look for tumor in the pancreas and other organs. As shown in FIG. 1A, extensive tumor growth is evident throughout the pancreas. The same tumor nodule in the liver indicated by an arrow in 1A exhibits intense β-galactosidase expression in 1B. 1A=gross necropsy; 1A=tissues after staining for β-galactosidase. Metastases were present in various organs in four of five mice including the spleen, liver, lung, adrenal gland and even within the diaphragm. This experiment was repeated with similar results.

To establish selective targeting tumor and metastasis, prior to sacrificing the mice, the TfRscFv-LipA complex carrying pSVb (LacZ) plasmid DNA for β-galactosidase expression was i.v. injected into the mice three times over a 24 hour period (40 µg of plasmid DNA per injection). All five mice were sacrificed 60 hours post-injection and various organs including the liver, lung, spleen, pancreas and diaphragm were harvested and examined for the presence of metastasis and tumor specific staining. Fresh samples, sliced at 1 mm thickness, were stained with X-gal to produce a blue color where the gene is expressed. The tumor targeting ability and high transfection efficiency of the complex is demonstrated by the presence of the reporter gene in the various organs from this animal (FIG. 1B). In the liver, lung, adrenal gland and diaphragm it is clearly shown that the reporter gene is highly expressed only in the metastases, while no blue color is evident in the adjacent normal tissue. The metastasis visible in the liver in FIG. 1A (arrow) is the same tumor nodule strongly expressing β-galactosidase in FIG. 1B (arrow) confirming the tumor specific nature of this nanocomplex. In some of the mice, growth of the tumor in pancreas also resulted in extrusion of tumor through the original incision site used for implantation. In FIG. 1B this strongly blue stained subcutaneous tumor, surrounded by normal non-stained skin is also shown, again showing tumor cell specificity. Similar results were observed in the rest of the mice, and in the repeat experiment. Thus, this systemically administered nanocomplex will target tumor cells both primary and metastatic, wherever they occur in the body, and efficiently deliver plasmid DNA. We wished to expand the potential of this delivery system to include contrast agents. The ability to do so could result in improved imaging and cancer detection.

In vitro Studies Using TfRscFv-Lip Complex to Deliver Magnevist®

As Magnevist® is one of the most frequently employed contrast agent in the clinic, it was chosen as for use in these studies. In these initial experiments, it was examined whether the complex could be prepared with Magnevist® and if doing so would enhance the MRI signal. Since trypsinization could lead to membrane damage and leakage of contrast agent from the cells, adherent cells were not employed in these studies. Instead, a human lymphoblastic leukemia cell line, K562, which grows as a suspension culture was used. Moreover, gentle pelleting and washing of the cells would remove any excess Magnevist® or complex prior to imaging, allowing only cell associated signal to be detected.

1. Time Dependent Image Enhancement by the TfRscFv-Lip-Mag Nanocomplex

The optimal time for transfection of the TfRscFv-Lip-Magnevist® nanocomplex was examined. The suggested clinical dose of Magnevist® is 0.1 mMole/kg. In these initial studies a dose of 0.3 mMole/kg was used (corrected for the smaller weight and blood volume of mouse versus man) in the complex per 250 µl of transfection solution. K562 cells were transfected for times ranging from 20 to 90 minutes. Twenty minutes showed very low transfection activity based upon the image intensity. However, as shown in FIG. 2A, by sixty minutes the cells transfected with the complex showed a large increase in intensity as compared to the untreated cells. The intensity of the untreated cells (202±48) was not significantly different than that of an empty marker tube (194±43) indicating that the cells themselves do not contribute to the signal detected. More importantly, the transfection efficiency plateaus at approximately 60 minutes since the relative intensity of the cells transfected for 60 and 90 minutes were identical (317±46 and 317±47, respectively).

2. Magnevist® Dose Dependent Image Enhancement

Figure 2B:
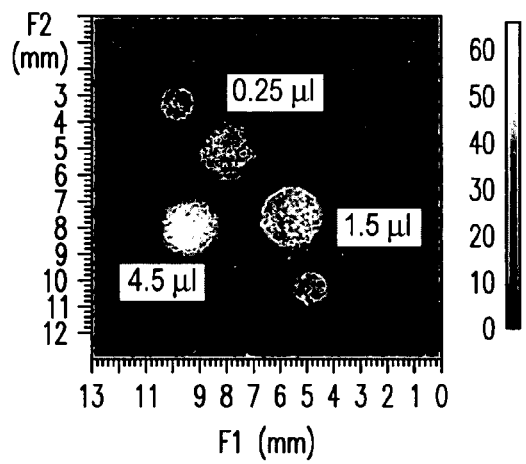

Using 60 minutes as the transfection time, the effect of increasing amounts of Magnevist® on the TfRscFv-Lip-Mag complex image enhancement was then assessed. The doses tested were 0.05, 0.3 and 0.9 mMole/kg. Corrected for size and blood volume of the mouse, the volumes of Magnevist® used in the complex per 250 ul of transfection solution were 0.25 µl, 1.5 µl and 4.5 µl. As shown in FIG. 2B and Table 1, the image intensity increases and the T1 relaxation time shortens as a function of the amount of contrast agent included in the complex.

TABLE 1

Relative Intensity and T1 Relaxation Time as a Function of Magnevist ® in the Immunoliposome Complex

| Dose of Contrast Agent (mM/kg) | Relative Intensity | T1 (seconds) |
|---|---|---|
| 0.05 (0.25 µl) | 293 ± 50 | 1.43 ± 0.007 |
| 0.3 (1.5 µl) | 379 ± 43 | 1.16 ± 0.004 |
| 0.9 (4.5 µl) | 454 ± 51 | 1.01 ± 0.004 |

3. Image Enhancement by TfRscFv-Lip-Mag as Compared to Free Magnevist®

Figure 2C:
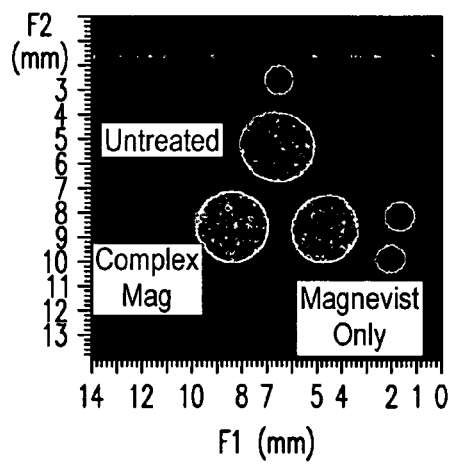

Based upon the above experiments, it was shown that the TfRscFv-Liposome can complex with Magnevist® and deliver it to the cells for image enhancement. To assess the level of enhancement of the complexed contrast agent as compared to the agent alone and demonstrate that the signal obtained is not due to the presence of unincorporated Magnevist®, K562 cells were treated with either free Magnevist® or the TfRscFv-Lip-Mag nanocomplex. The identical amount of contrast agent (0.3 µM/kg or 1.5 µl/250 µl transfection volume) and transfection time (60 minutes) was used for both solutions. While free Magnevist® showed enhanced contrast relative to the untreated cells as expected, the cells treated with the TfRscv-Lip-Mag complex demonstrated a much greater increase in image intensity and shortened Ti relaxation time compared to both untreated and free Magnevist® treated cells (FIG. 2C, Table 2). These results not only demonstrate the increased efficiency of contrast agent uptake by means of the targeted nanocomplex, but also indicate that the observed signal is likely not due to uncomplexed Magnevist®.

TABLE 2

Comparison of the Relative Intensity and T1 Relaxation Time Between Free and Immunoliposome Complexed Magnevist ®

| Treatment | Relative Intensity | T1 (seconds) |
|---|---|---|
| Untreated | 455 ± 47 | 1.80 ± 0.009 |
| Free Magnevist ® | 538 ± 50 | 1.51 ± 01007 |
| Immunliposome Complexed Magnevist ® | 662 ± 52 | 1.40 ± 0.004 |

In Vivo Image Enhancement With TfRscFv-Lip-Mag

The above studies established that the nanocomplex could more efficiently image tumor cells in vitro than Magnevist® alone. However, to have potential for clinical use, the complex must exhibit a similar effect in vivo. The same human pancreatic cancer orthotopic mouse model (CaPan-1) was used for these studies as was used above to demonstrate tumor specific targeting of the complex carrying a reporter gene. In addition, a second tumor model, a subcutaneous prostate xenograft mouse model (DU145) was also used. Mice bearing CaPan-1 or DU145 tumors were imaged on a 7T Bruker NMR as described in Methods. Once positioned in the coil, a baseline image was obtained using a TI-weighted Turbo RARE (rapid acquisition with rapid enhancement) three-dimensional imaging sequence. To facilitate image alignment, after baseline acquisition the animal was maintained in the animal holder while the imaging solution was administered via intravenous injection. Signal acquisition was begun within three minutes of the injection. The amount of Magnevist® administered to the mouse, either free (as is performed in the clinic) or included in the complex was 10 µl. This amount is equivalent to 0.2 mM/Kg or twice what is used in humans. This amount was selected since the standard human dose of 0.1 mM/Kg Magnevist® alone gave a very poor signal in the mice. The imaging with free Magnevist® and the TfRscFv-Lip-Mag complex were performed on two consecutive days. A baseline scan was also performed prior to administration of nanocomplex to confirm that all of the Magnevist® from the previous day had been washed out. MR technique and windows were consistent between the two sets of images with the windows adjusted to correct for an automatic windowing feature of the scanner.

Figures 3A, 3D, 3G:
Figures 3B, 3E, 3H:
Figures 3C, 3F, 3I:

Images of the Magnevist® and nanocomplex-Mag in three separate mice are show in FIG. 3A-I. In FIG. 3A, 3D and 3G, four months after surgical implantation of the CaPan-1 tumor cells, the animal is carrying a large orthotopic tumor. The increased resolution and signal intensity, as compared to the contrast agent alone is quite evident. Similar results are observed in the second mouse with a CaPan-1 tumor shown in FIG. 3B, 3E and 3H. This animal, only two months post-surgery, has a visible subcutaneous tumor growing through the site of the incision. A small abdominal mass was also detected by palpation. Not only is the signal in the subcutaneous tumor more enhanced after administration of the complexed Magnevist®, but what appears to be the small orthotopic tumor (arrow) is evident in this scan and not in the one in which the animal received the free Magnevist®. Similarly, increased definition and contrast are evident in the subcutaneous DU145 tumor (FIG. 3C, 3F and 3I) after injection with the TfRscFv-Lip-Mag complex as compared to the free Magnevist®. Reconstruction and quantitation was performed on the images in FIG. 3B, 3E and 3H and 3C, 3F and 3I, representing the two different tumor models, Pancreatic cancer (CaPan-1) and Prostate cancer (DU145). In both instances, there is an increased intensity (pixels) by the free Magnevist® over the baseline, as expected. However, delivery of the imaging agent by the tumor targeting nanocomplex results in an almost three-fold further increase in signal intensity in both of these tumor models. These studies thus demonstrate that when Magnevist® is incorporated within the TfRscFv-Liposome complex there is an improved tumor visualization in an in vivo situation, and they suggest the potential benefit of further developing this means of tumor detection for clinical use.

Physical Characterization Studies

While the in vitro studies offered evidence that complexed Magnevist® is encapsulated within the liposome, sophisticated microscopy techniques (SEM and SPM) have confirmed this and further characterize (e.g. complex size) the TfRscFv-Lip-Mag complex.

1. Imaging of liposomes without Magnevist®

High-resolution imaging implies narrow depth of focus and so requires relatively thin and flat samples. How thin varies with technique, but surface and substrate effects—surface energy and symmetry lowering—often dominate the structural forces typical of biomaterials. This is particularly true in the case of liposomes given their tenuous nature. (Foo, J. J., et al., *Annals of Biomedical Engineering* 31:1279-1286 (2003)). So an understanding of reliable methods for preparing and characterizing the dimensional and mechanical stability of isolated liposomes is an essential step. The goal of this characterization is to perform direct sensing of the mechanical stiffness and magnetic properties of nanoparticles to establish that the contrast agent is indeed contained within the nanoparticle and not simply associated externally with the liposomes.

Figure 4A:
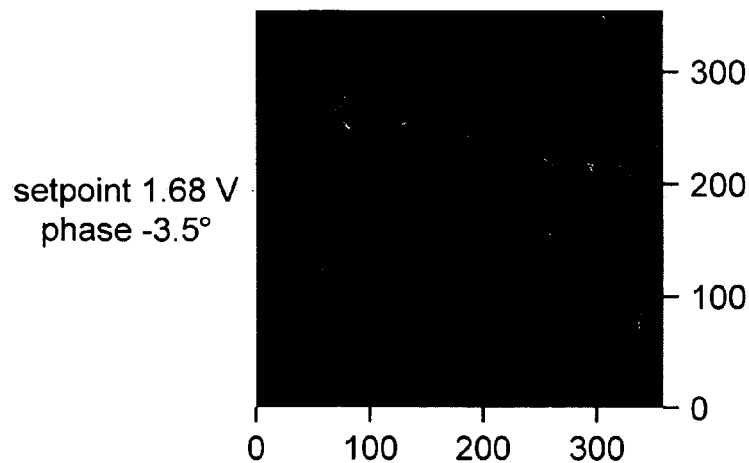
Figure 4B:
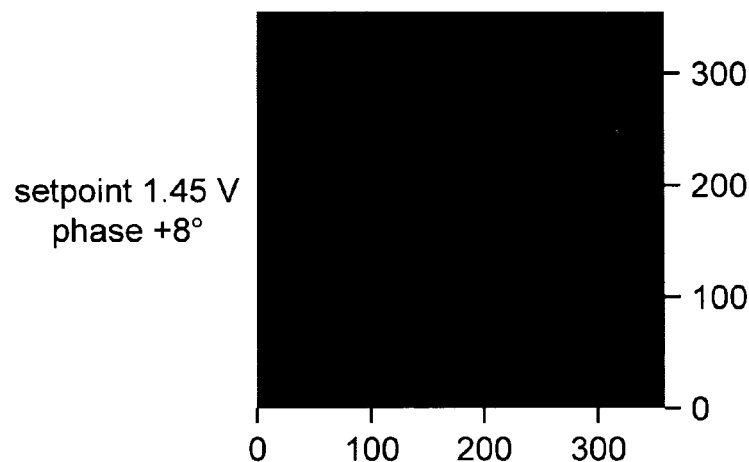
Figure 4C:
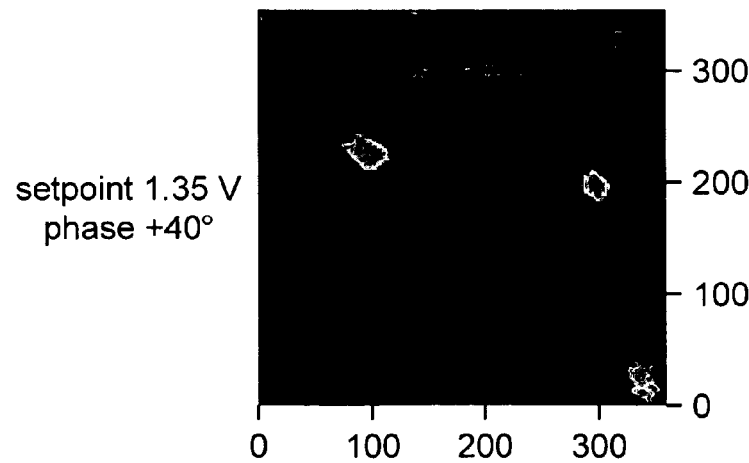

The SPM images surface topography in tapping mode by oscillating the tip and cantilever to which it is attached close to the cantilever resonance frequency. A feedback circuit maintains the oscillation of the cantilever at a constant amplitude. This constant amplitude is given a by a set point which is somewhat smaller than that of the freely oscillating cantilever. Since the SPM tip interacts with the surface through various small forces, there is a phase shift between the cantilever excitation and its response at a given point on the surface. For an inhomogeneous surface, the tip-surface interactions will vary according to surface charge, steep topographical changes, and mechanical stiffness variations, for example. By changing the set point and observing how certain features respond to softer or harder tapping, we can correlate this with the response expected for a specific structure such as a liposome. (The free oscillation amplitude signal is approximately 1.78 V.) A sequence of SPM phase images of a pair of isolated liposomes without payload is shown in FIG. 4A-C. FIG. 4A was imaged at a set point of 1.68 V and the corresponding negative phase difference between the substrate and liposome indicates that the tip-sample interaction is attractive for the liposome, given by a phase value of −3.5 degrees. In the case of an attractive interaction and negative phase, the phase image of the liposome appears dark, except for a topographically keyed ring at the liposome edge. FIG. 4B demonstrates the effect of reducing the set point to 1.45 V: The liposome now appears bright since the tip-sample interaction becomes repulsive, and in this case the phase difference between the liposome and substrate is +8 degrees. Finally, FIG. 4C shows that the phase difference recorded at a set point of 1.35 V increases further, becoming +35 degrees.

2. Imaging of liposome-encapsulated Magnevist®

FIG. 5A-C presents SPM and SEM images of isolated liposome-encapsulated Magnevist (Lip+Mag) nanoparticles. The size distribution of single Lip+Mag particles is in the range of 100-200 nm diameter and scales according to optical measurements that indicate that payload-encapsulating liposomes are approximately 50% larger than liposomes alone in their spherical state.

The SPM topograph appearing in FIG. 5A indicates that liposomes containing Magnevist® have a bimodal surface shape after drying that is more complex than that of the simple elliptical surface of a liposome containing no payload (not shown). The SPM phase behavior differs markedly from that of payloadless liposomes, the outer ring is repulsive relative to the center, and a corresponding SPM phase image is shown in FIG. 5B. Regions of both attractive and repulsive tip-sample interaction appear at moderate set point values. A correlation between the SPM phase image obtained at a set point of 1.6 and the SEM image in TE mode is evident in FIGS. 5B and 5C. Liposomes appear uniformly bright across the entire particle in SEM images (not shown), similar to the uniform phase images we obtain by SPM. Tips and cantilevers change with time and usage. Moreover, it is important to verify that the images produced are not affected by tip instabilities due to foreign material on the tip. Thus, they are changed frequently. Since each cantilever is somewhat different with respect to its resonance properties, the set points used in FIGS. 4 and 5 are different.

3. Imaging of TfRscFv-Lip-Mag Nanocomplex

Figure 6A:
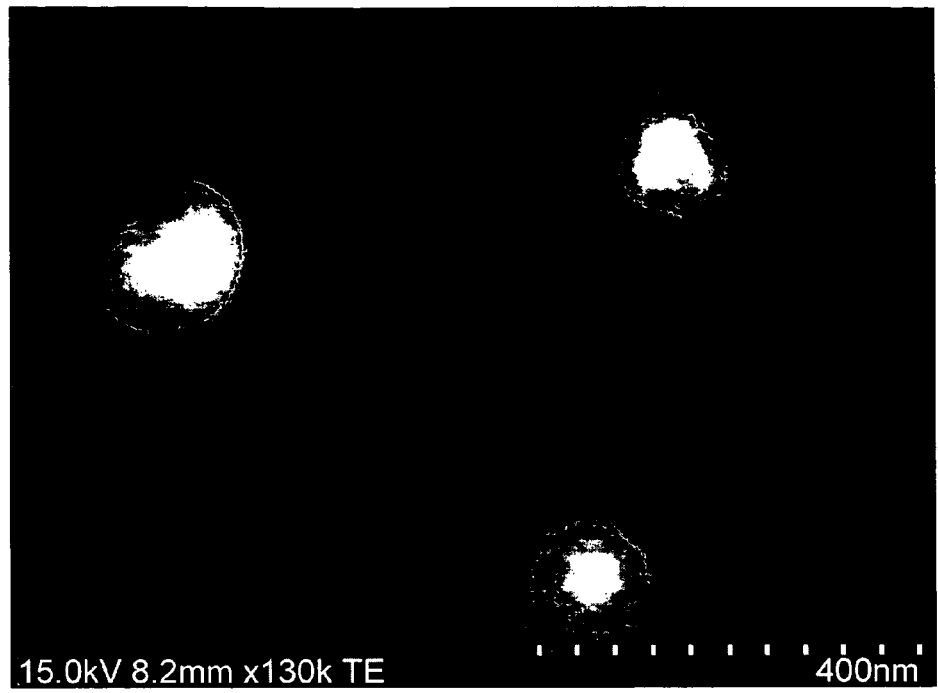
Figure 6B:
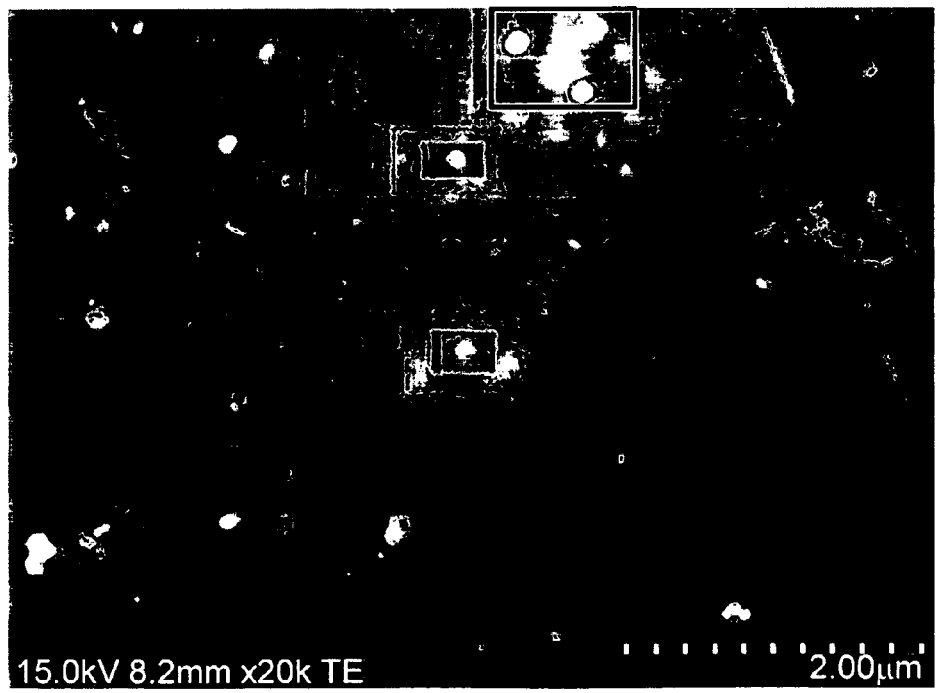

The complete TfRscFv-Lip-Mag nanocomplex was prepared and imaged by SEM and SPM as described in Methods. Results, shown in FIG. 6A and 6B indicate that the solvent film undergoes phase separation; however, examples of isolated NDS can be readily observed on the dried film. Note that the SEM beam clearly causes some damage to the film, but the particles can be repeatedly scanned several times before beam damage becomes significant. The appearance of the full complex is different from that of the (Lip+Mag) only. The shape is less regular, and considerable texturing of the liposome surface following drying is consistent with protein denaturation. Also, SEM TE images indicate that the well-defined boundary between the outer ring and center of the liposome seen with the (Lip+Mag) particles is less apparent and the shape much more variable. This is consistent with the view that the presence of protein within the liposome has altered the osmotic outflow across the liposome during film drying.

Figure 7A:
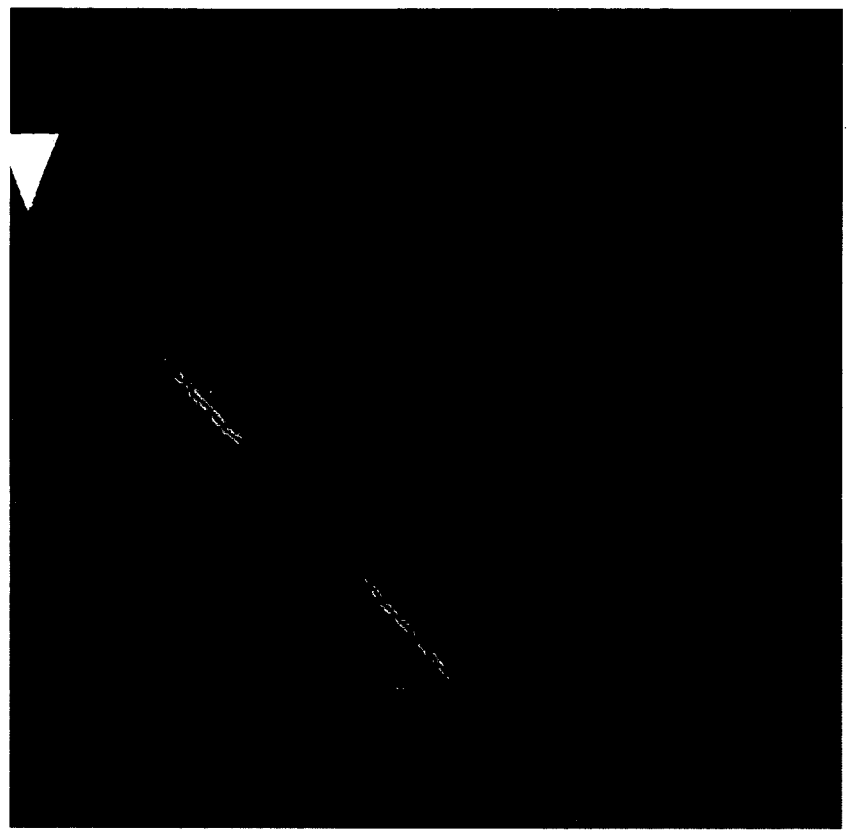
Figure 7B:
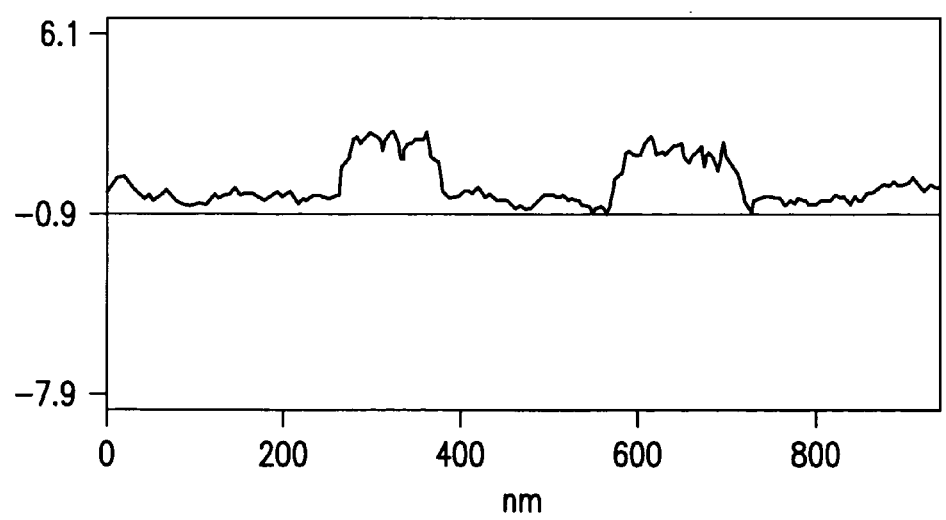
Figure 8A:
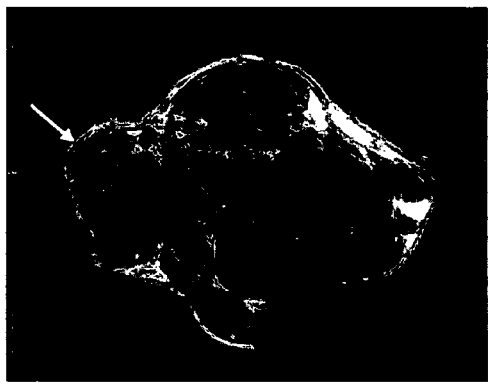
Figure 8B:
Figure 8C:
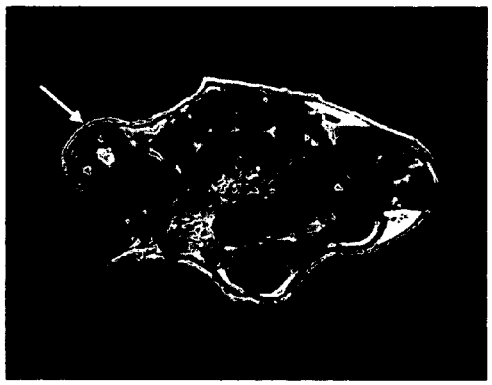
Figure 8D:
Figure 8E:
Figure 8F:
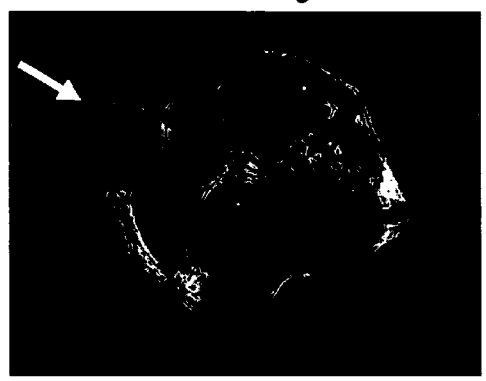
Figure 8G:
Figure 8H:

It is possible to obtain additional information about these NDS particles by using the magnetic force microscopy imaging capabilities of the SPM (MFM). Since the magnetic moment of gadolinium-containing Magnevist® is quite large, it should be possible using a magnetized SPM tip to interact with the oriented Magnevist® concentrated within the liposomes. This is shown in FIG. 7A and 7B for MFM of several approximately 100-200 nm diameter nanocomplexes. By using the lift-mode capabilities of the SPM it is established that the produced image is truly magnetic in nature. In this mode, a topographic image under normal tapping mode conditions is obtained. The reference surface information is then used to offset the tip by a specified height away from the surface and the surface is then scanned at this increased height. This removes the influence of topography on the signal. MFM images obtained in lift-mode at a height of 15 nm or more from the surface are given by the magnetic phase image. The appearance of a signal confirms the presence of gadolinium encapsulated within the complex. FIG. 7A is an SPM topographic/magnetic phase image of the full TfRscFv-Lip-Mag nanocomplex. The appearance of a double dipole-like signal in FIG. 7B consisting of attractive and repulsive in-plane magnetic interactions suggests that the cause of this interaction is the nonuniform toroidal distribution of Magnevist® within the NDS, consistent with SEM and nonmagnetic SPM phase images.

Discussion

The results described herein demonstrate that we can encapsulate and deliver the commonly used MR imaging agent Magnevist®, to tumor cells both in vitro and in an orthotopic animal model and in doing so produce a more defined and intense image than seen with uncomplexed Magnevist®.

As shown in FIG. 1, the nanocomplexes of the present invention can target metastatic disease, thereby enhancing detection sensitivity for metastases. Using SEM and SPM it has been demonstrated that the TfRscFv-liposome complex maintains its nanometer size when Magnevist® is encapsulated (particles of approximately 100-200 nm are shown in FIGS. 6 and 7). It has also been demonstrated that the structural and mechanical properties of liposomes containing a payload are sufficiently different from those without one, thereby confirming that Magnevist® is indeed encapsulated with the liposome. This was further confirmed by MFM imaging of the complex.

While not wishing to be bound by the following theory, a tentative explanation for the internal structure of (Lip+Mag) is that the slight bulge in the SPM topographic image, represents a liposome-confined phase separation, i.e., formation of a dense Magnevist® lipid toroidal distribution around the periphery of the particle with an preferential aqueous phase at the particle's center. This response is probably attributable to several important factors: First, the properties of Magnevist® solution are pH ~6.5-8, an osmolality of 1,960 and viscosity of 4.9 at 20° C. according to the manufacturer. A plausible chemical basis for this separation of the solution noted in the Magnevist® data sheet: The meglumine salts dissociate completely from the complex, so changes in the local osmotic conditions. Coupled with the charge interaction of the gadolinium complex and cationic lipid, these interactions may provide a strong driving force for a hypertonic phase separation within the liposome. The charge distribution between the cationic lipid and Magnevist® solution is effective at stabilizing the liposome and providing structural support in solution, and apparently in the bloodstream. This enhanced structural support is an important benefit for these studies since it allows most particles to remain intact during the film drying process, in contrast to the extensive decomposition observed with the liposome only solutions.

The foregoing Examples demonstrate the successful encapsulation of an MR contrast agent in the immunoliposome complexes of the present invention. The image enhancement demonstrated by the complexes over conventionally delivered Magnevist® indicates the ability of this system to improve early detection of cancer via MRI.

EXAMPLE 2

Comparison of Imaging in Different Cell Lines

FIGS. 8A-8H show improved MR imaging in two different models of cancer using the Ligand-HK-Liposome-Mag nanocomplex. Nanocomplexes for use in this Example were prepared using the same ratios and procedures as set forth in Example 1. Human breast cancer MDA-MB-435 (FIG. 8E-8H) or human prostate cancer cell line (DU145) (FIG. 8A-8D) cells were subcutaneously injected on the lower back, of female athymic nude mice. Free Magnevist®, or the TfRscFv-liposome nanocomplex (scLip-Mag), or the TfRscFv-HK-liposome nanocomplex (scLip-HK-Mag) comprising the HoKc peptide, containing the same dose of Magnevist® were i.v. injected (via the tail vein) into each of the three mice on three consecutive days. This amount of Magnevist® is equivalent to twice the dose that would be administered to a human patient. The total volume of solution administered in all cases was 400 µl. A baseline scan was performed just prior to administration of both nanocomplexes to confirm that all of the Magnevist® from the previous day had been washed out. MR technique and windows were constant between the four sets of images with the windows adjusted to correct for an automatic windowing feature of the scanner. The panel shows the difference in MRI signal in a mouse with a subcutaneous tumor in which the increased definition and contrast are evident in both the prostate tumor (DU145) (FIG. 8A-8D) and the breast tumor (435) (FIG. 8E-8H) after injection with the scLip-Mag and even more so after injection with the scLip-HK-Mag.

FIG. 9A-9C shows tumor-specific targeting of a CaPan-1 subcutaneous tumor and orthotopic metastasis model by the TfRscFv-HK-Liposome-Mag nanocomplex. Subcutaneous CaPan-1 xenograft tumors were induced in female athymic nude mice as described in Methods in Example 1. The tumors were harvested and a single cell suspension in MATRIGEL® was injected into the surgically exposed pancreas. Eight weeks post injection the TfRscFv-Liposome complex with or without HoKC (HK) peptide carrying Magnevist® was injected into the mouse on two consecutive days. The total volume of solution administered in all cases was 400 µl. A baseline scan was performed just prior to administration of the nanocomplex to confirm that all of the Magnevist® from the previous day had been washed out. MR technique and windows were constant between the three sets of images with the windows adjusted to correct for an automatic windowing feature of the scanner. Similar to FIG. 8A-8H, improved imaging resolution of subcutaneous tumor (white arrow) and the metastatic lesions is observed, as shown in Table 3.

TABLE 3

Intensity Increase over Baseline by Free and Complexed Magnevist

| | Sample | |
|---|---|---|
| | CaPan-1 | DU145 |
| | % Increase Over Baseline | |
| Complexed Magnevist ® | 99 | 215 |
| Free Magnevist ® | 34.5 | 70 |

EXAMPLE 3

Comparison of Dynamic MRI Scans of Subcutaneous PANC-1 Tumors after Systemic Injection of Free (Uncomplexed) or TJRScFv-Lip-Magnevist The following experiments were performed to compare the rate and level of uptake and washout between free (uncomplexed) and TfRscFv-Lip-Mag in tumors after systemic delivery. Subcutaneous xenograft tumors of PANC-1 were induced in female athymic nude mice by injection of 1 to $2\times10^7$ PANC-1 cells suspended in Matrigel TM collagen basement membrane matrix (BD Biosciences). Approximately 2.5-3 weeks later, the animals were used for imaging. Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). The targeting moiety used in these studies is the anti-transferrin receptor single chain antibody fragment (TfRscFv).

To encapsulate the imaging agent, the TfRscFv was mixed with the liposome at a specific ratio and incubated at room temperature for 1-30 minutes, suitably 5-20 minutes, most suitably 10-12 minutes. Magnevist® was added to this solution, mixed and again incubated at room temperature for 1-30 minutes, suitably 5-20 minutes, most suitably 10-12 minutes. When prepared for in vivo use, sucrose or dextrose was added to a final concentration of 0.5-50%, suitably 1-20%, most suitably 10% for sucrose and 5% for dextrose, and incubated at room temperature for 1-30 minutes, suitably 5-25 minutes, most suitably 15-20 minutes. The complex is formed at a ratio of 1 mg imaging agent to 0.33-1.17 ug TfRscFv to 10-35 ug Liposome (suitably 1 mg imaging agent to 0.5 to 1.0 ug TfRScFv to 14-28 ug Liposome, most suitably 1 mg imaging agent to 0.71 ug TfRscFv to 21 ug Liposome) using the above procedure. A range of acceptable sizes of the complex is from about 20 to 1000 nm, suitably about 50 to 700 nm and most suitably about 100 to 500 nm. Here the complex was formed using 4.7 mg Magnevist, 99 ug Liposome and 3.3 ug TfRscFv with dextrose to a final concentration of 5%.

A mouse bearing PANC-1 subcutaneous tumors induced as above was anesthetized and placed in an animal holder system. Anesthesia was induced using isoflurane at 4%, with the remaining gas comprising a 66% oxygen and 30% nitrous oxide mixture. Maintenance of anesthesia was achieved with 1.0 to 2.0% isoflurane (preferably 1.5%) under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted two dimensional Turbo RARE (rapid acquisition with rapid enhancement) imaging sequences performed on a 7T Bruker BioSpin (Germany/USA) imaging console. The imaging parameters used were: T1-weighted 2D (2-dimensional), TE 10.21 ms, TR 420.3, Flipback off, 8 echoes with a field of view of 5.12/5.12 cm. After a baseline image was acquired, the animal was kept immobilized in the animal holder and either the free (uncomplexed) Magnevist® (Mag, or gad-d herein) or the TfRscFv-Lip-Mag complex containing the identical amount of Mag (total volume 50-1000 ul, suitably 100-500 ul, most suitably 200-400 ul) was systemically administered using a 27G needle by intravenous injection into the tail vein of the animal and the imaging sequence was immediately initiated. The scan (2 averages, 1.3min) was repeated periodically over two hours and the pixel intensity measured and plotted. The same mouse was used for imaging with both the free and the complex. The imaging was performed on sequential days, with the Free Mag first.

Figure 10:
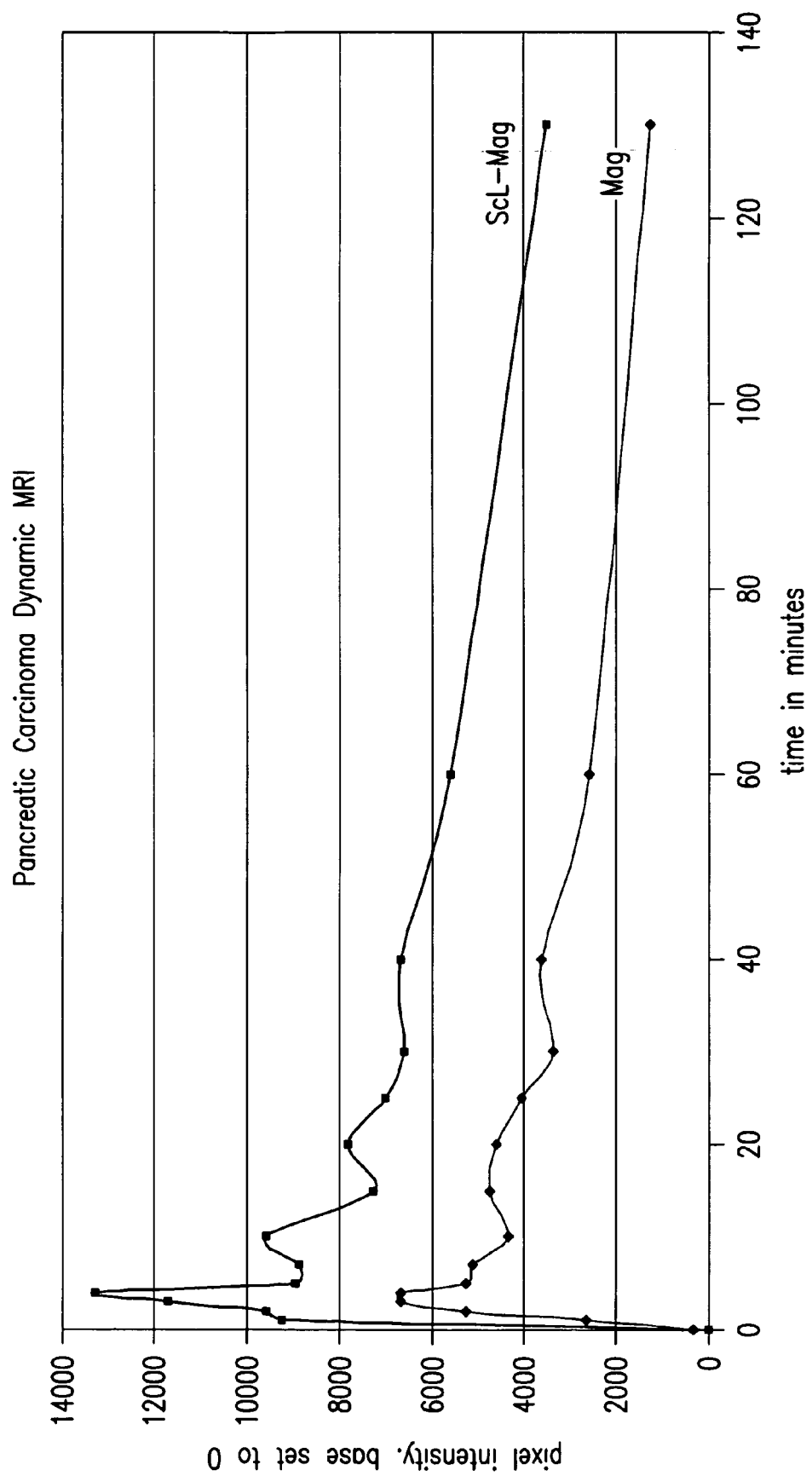
FIG. 10 shows dynamic MRI showing the increase in intensity using Mag-delivered by the complexes of the present invention in a pancreatic carcinoma model, as compared to free Mag.
Figure 12E:
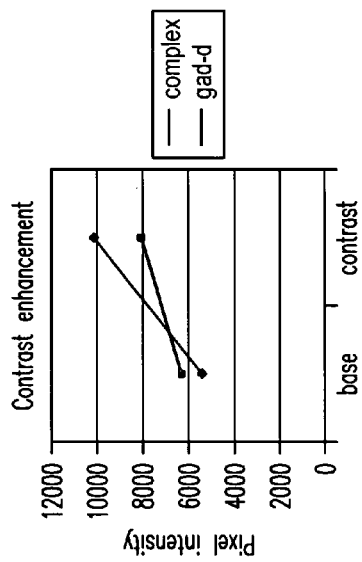
FIG. 12A-12E shows a greater enhancement in MR imaging of lung metastases by Mag-comprising complexes of the present invention.
Figure 12A:
Figure 12C:
Figure 12B:
Figure 12D:
Figure 14B:
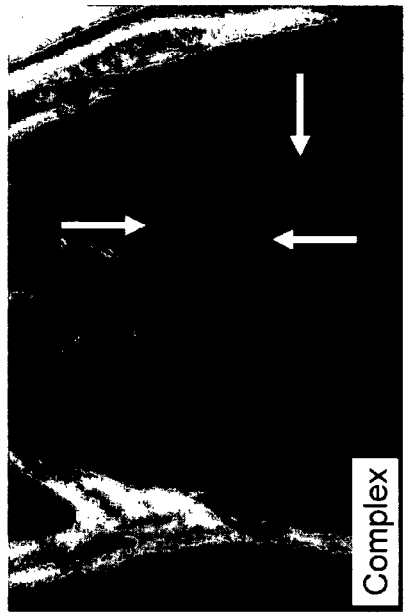
FIG. 14A-14D shows greater sensitivity of detection by MR imaging of small renal cell carcinoma lung metastases by Mag-comprising complexes of the present invention.
Figure 14D:
Figure 14A:
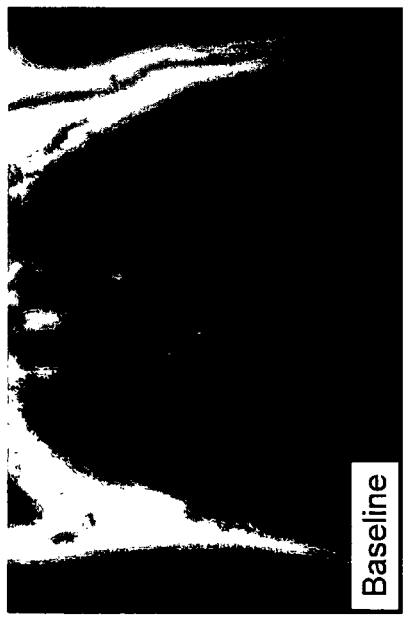
Figure 14C:
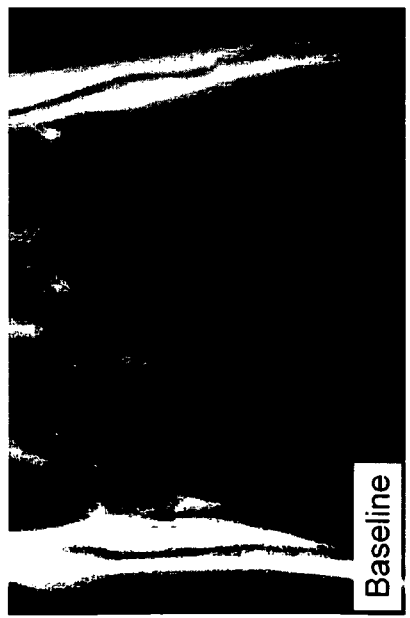

As Shown in FIG. 10, there is a significantly higher level signal in the tumor after intravenous injection of the complex as compared to the free imaging agent. More significantly, this higher level is maintained over the time course of the experiment.

EXAMPLE 4

Detection of CaPan-1 Liver Metastasis by TfRscFv-Lip-HoKC-Magnevist

The following experiments were performed to assess the ability of the TfRscFv-Lip-HoKC-Mag complex of this invention to detect and enhance imaging of metastatic tumors. As an example, metastases from a pancreatic cancer was examined, however, imaging of metastases from any type of cancer can be achieved using the complexes and methods of the present invention (e.g. prostate, melanoma, renal, breast, gastric, liver, ovarian, bladder, head and neck, brain, bone and any other type of solid tumor). Subcutaneous xenograft tumors of CaPan-1 were induced in female athymic nude mice by injection of 0.5 to $1 \times 10^7$ CaPan-1 cells suspended in Matrigel™ collagen basement membrane matrix (BD Biosciences). Approximately eight weeks later the tumors were harvested and a single cell suspension of the tumor was prepared. $1.2$-$1.5 \times 10^7$ cells, also suspended in Matrigel™, were injected into the surgically exposed pancreas of female athymic nude mice as previously described (Alisauskus, R., Wong, G. Y., and Gold, D. V., Initial studies of monoclonal antibody PAM4 targeting to xenografted orthotopic pancreatic cancer, *Cancer Research* 55, 5743s-5748s (1995)).

Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). The HoKC peptide {K[K(H)KKK]$_5$-K(H)KKC} (SEQ ID NO:1) carries a terminal cysteine to permit conjugation to a maleimide group. Thus, when the HoKC peptide was used, the liposome formulation also included N-maleimide-phenylbutyrate-DOPE (MPB-DOPE) at 0.1 to 50 molar percent of total lipid, more preferably 1-10 molar percent of total lipid, most preferably 5 molar percent of total lipid. The HoKC liposomes were prepared as previously described (Yu, W. et al. Enhanced transfection efficiency of a systemically delivered tumor-targeting immunolipoplex by inclusion of a pH-sensitive histidylated oligolysine peptide, *Nucleic Acids Research* 32, e48 (2004)). The targeting moiety used in these studies is the anti-transferrin receptor single chain antibody fragment (TfRscFv).

To encapsulate the imaging agent, the TfRscFv was mixed with the liposome at a specific ratio and incubated at room temperature for 1-30 minutes, suitably 5-20 minutes, most suitably 10-12 minutes. Magnevist® was added to this solution, mixed and again incubated at room temperature for 1-30 minutes, suitably 5-20 minutes, most suitably 10-12 minutes. When prepared for in vivo use, sucrose or dextrose was added to a final concentration of 0.5-50%, suitably 1-20%, most suitably 10% for sucrose and 5% for dextrose, and incubated at room temperature for 1-30 minutes, suitably 5-25 minutes, most suitably 15-20 minutes. The complex is formed at a ratio of 1 mg imaging agent to 0.33-1.17 ug TfRscFv to 10-35 ug Liposome-HoKC (suitably 1 mg imaging agent to 0.5 to 1.0 ug TfRScFv to 14-28 ug Liposome-HoKC, most suitably 1 mg imaging agent to 0.71 ug TfRscFv to 21 ug Liposome-HoKC) using the above procedure. A range of acceptable sizes of the complex is from about 20 to 1000 nm, suitably about 50 to 700nm and most preferable 100 to 500 nm. Here the complex was formed using 4.7 mg Magnevist®, 99 ug Liposome-HoKC and 3.3 ug TfRscFv with dextrose to a final concentration of 5%.

Mice bearing CaPan-1 orthotopic tumors induced above (approximately 12 weeks post-surgical implantation of the tumor cells) were anesthetized and placed in an animal holder system. Anesthesia was induced using isoflurane at 4%, with the remaining gas comprising a 66% oxygen and 30% nitrous oxide mixture. Maintenance of anesthesia was achieved with 1.0 to 2.0% isoflurane (preferably 1.5%) under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted Turbo RARE (rapid acquisition with rapid enhancement) three-dimensional imaging sequences performed on a 7T Bruker BioSpin (Germany/USA) imaging console. The imaging parameters used were: T1-weighted Turbo-RARE 3D (3-dimensional), TE 13.3 ms, TR 229.5 ms, Flipback on, 4 echoes with a field of view of 8.0/3.5/3.5 cm and a 256×256×256 matrix. After a baseline image was acquired, the animal was kept immobilized in the animal holder and the TfRscFv-Lip-HoKC-Mag complex (total volume 50-1000 ul, more preferably 100-500 ul, most preferably 200-400 ul) was systemically administered using a 27G needle by intravenous injection into the tail vein of the animal and the 3D imaging sequence was immediately initiated.

After imaging, the animal was euthanized and visually examined for the presence of metastases. The liver was removed, fixed in Formalin, paraffin embedded, sectioned and stained using H&E using standard procedures well know to one of ordinary skill in the art. The sections were examined by microscope and the observed metastasis photographed.

FIG. 11A-11A: FIG. 11A: pre-contrast. FIG. 11B: TfRcFv-Lip-HoKC-Mag injection, FIG. 11C: histology. The orthotopic pancreatic cancer shows enhancement with TfRcFv-Lip-HoKC-Mag (short white arrows). The two areas identified with the short white arrows are connected on more posterior slices and represent the primary orthotopic placed tumor. A small metastasis (thick white arrows) enhances in the same pattern seen with the primary tumor. The thin extension of liver (long thin arrow) lies adjacent to the metastasis. Necropsy (not shown) and histology (right image) confirm presence of metastasis (black arrows) directly adjacent to long thin extension of liver. Note the similarity of shape of one of the pieces of metastatic tumor to the appearance on the MRI.

EXAMPLE 5

Enhanced Detection of Lung Metastasis by TfRscFv-Lip-Magnevist

The following experiments were performed to demonstrate that when administered intravenously (or via any other appropriate route, e.g., but not limited to IT, ID, IM, IP) the complexes of the present invention carrying an imaging agent can enhance detection of metastases as compared to when the imaging agent is administered without the use of the complex. Lung tumors were induced in female Balb/C mice by the intravenous injection of 1 to $10 \times 10^4$ RenCa cells. This method results in metastases that reside almost exclusively in the lungs of the animals and thus serves as a model system for any other type of cancer that results in lung tumors either as primary disease or as metastases. Approximately 2-4 weeks later the animals were used for imaging.

Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). The targeting moiety used in these studies is the anti-transferrin receptor single chain antibody fragment (TfRscFv).

To encapsulate the imaging agent, the TfRscFv was mixed with the liposome at a specific ratio and incubated at room temperature for 1-30 minutes, suitably 5-20 minutes, most suitably 10-12 minutes. Magnevist® was added to this solution, mixed and again incubated at room temperature for 1-30 minutes, suitably 5-20 minutes, most suitably 10-12 minutes. When prepared for in vivo use, sucrose or dextrose was added to a final concentration of 0.5-50%, suitably 1-20%, most suitably 10% for sucrose and 5% for dextrose, and incubated at room temperature for 1-30 minutes, more suitably 5-25 minutes, most suitably 15-20 minutes. The complex is formed at a ratio of 1 mg imaging agent to 0.33-1.17 ug TfRscFv to 10-35 ug Liposome (suitably 1 mg imaging agent to 0.5 to 1.0 ug TfRScFv to 14-28 ug Liposome, most suitably 1 mg imaging agent to 0.71 ug TfRscFv to 21 ug Liposome) using the above procedure. A range of acceptable sizes of the complex is from about 20 to 1000 nm, suitably about 50 to 700 nm and most suitably about 100 to 500 nm. Here the complex was formed using 4.7 mg Magnevist, 99 ug Liposome and 3.3 ug TfRscFv with dextrose to a final concentration of 5%.

A mouse bearing lung tumors induced above was anesthetized and placed in an animal holder system. Anesthesia was induced using isoflurane at 4%, with the remaining gas comprising a 66% oxygen and 30% nitrous oxide mixture. Maintenance of anesthesia was achieved with 1.0 to 2.0% isoflurane (preferably 1.5%) under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted two dimensional Turbo Multislice-Multiecho imaging sequence performed on a 7T Bruker BioSpin (Germany/USA) imaging console. The imaging parameters used were: T1-weighted 2D (2-dimensional), TE 10.21 ms, TR 400 ms, Flipback off, 8 averages with a field of view of 3.84×3.84 cm and a 256×256 matrix. After a baseline image was acquired, the animal was kept immobilized in the animal holder and either the free (uncomplexed) Magnevist® (gad-d) or the TfRscFv-Lip-Mag complex containing the identical amount of Mag (total volume 50-1000 ul, more suitably 100-500 ul, most suitably 200-400 ul) was systemically administered using a 27G needle by intravenous injection into the tail vein of the animal and the imaging sequence was immediately initiated. The pixel intensity of the images was measured and plotted. The same mouse was used for imaging with both the free and the complex. The imaging was performed on sequential days.

As Shown in FIG. 12A-12E, there is a significantly higher level signal in the tumor after intravenous injection of the complex as compared to the free imaging agent. Thus, the complex of this invention also enhances detection of relatively large metastases in the lung as compared to the currently used method of administering free imaging agent.

EXAMPLE 6

Enhanced Detection of Small Lung Metastasis by TjRscFv-Lip-Magnevist

The following experiments were performed to demonstrate that when administered intravenously (or via any other appropriate route, e.g., but not limited to IT, ID, IM, IP) the complexes of the present invention carrying an imaging agent can detect very small metastases that can not be detected when the imaging agent is administered without the use of the complex. Lung tumors were induced in female Balb/C mice by the intravenous injection of 1 to $10 \times 10^4$ RenCa cells. This method results in metastases that reside almost exclusively in the lungs of the animals and thus serves as a model system for any type of cancer that results in lung tumors either as primary disease or as metastases. Approximately 7-9 days later the animals were used for imaging.

Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). The targeting moiety used in these studies is the anti-transferrin receptor single chain antibody fragment (TfRscFv).

To encapsulate the imaging agent, the TfRscFv was mixed with the liposome at a specific ratio and incubated at room temperature for 1-30 minutes, suitably 5-20 minutes, most suitably 10-12 minutes. Magnevist® was added to this solution, mixed and again incubated at room temperature for 1-30 minutes, suitably 5-20 minutes, most suitably 10-12 minutes. When prepared for in vivo use, sucrose or dextrose was added to a final concentration of 0.5-50%, suitably 1-20%, most suitably 10% for sucrose and 5% for dextrose, and incubated at room temperature for 1-30 minutes, suitably 5-25 minutes, most suitably 15-20 minutes. The complex is formed at a ratio of 1 mg imaging agent to 0.33-1.17 ug TfRscFv to 10-35 ug Liposome (suitably 1 mg imaging agent to 0.5 to 1.0 ug TfRScFv to 14-28 ug Liposome, most suitably 1 mg imaging agent to 0.71 ug TfRscFv to 21 ug Liposome) using the above procedure. A range of acceptable sizes of the complex is from about 20 to 1000 nm, suitably about 50 to 700 nm and most suitably about 100 to 500 nm. Here the complex was formed using 4.7 mg Magnevist, 99 ug Liposome and 3.3 ug TfRscFv with dextrose to a final concentration of 5%.

A mouse bearing lung tumors induced above was anesthetized and placed in an animal holder system. Anesthesia was induced using isoflurane at 4%, with the remaining gas comprising a 66% oxygen and 30% nitrous oxide mixture. Maintenance of anesthesia was achieved with 1.0 to 2.0% isoflurane (preferably 1.5%) under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted two dimensional Turbo Multislice-Multiecho imaging sequence performed on a 7T Bruker BioSpin (Germany/USA) imaging console. The imaging parameters used were: T1-weighted 2D (2-dimensional) imaging sequence, TE 10.21 ms, TR 572.99ms, Flipback off, 8 averages with a field of view of 2.56×2.56 cm and a 256×256 matrix. After a baseline image was acquired, the animal was kept immobilized in the animal holder and either the free (uncomplexed) Magnevist® (gad-d) or the TfRscFv-Lip-Mag complex containing the identical amount of Mag (total volume 50-1000 ul, suitably 100-500 ul, most suitably 200-400 ul) was systemically administered using a 27G needle by intravenous injection into the tail vein of the animal and the imaging sequence was immediately initiated. The pixel intensity of the images was measured. The same mouse was used for imaging with both the free and the complex. The imaging was performed on sequential days. At this field of view 5 pixels is equivalent to approximately a 3 mm human tumor detected by CT.

As Shown in FIG. 13A-13D, a metastasis of 4 pixels (lower arrow) (which corresponds to a metastasis of approximately 0.4 mm in diameter) was detectable after injection with the complex but not after the free gad-d. Moreover the signal was significantly enhanced in a second slightly larger metastasis (upper arrow) as compared to the free gad-d. Thus, the complex of this invention also enhances detection of small metastases in the lung as compared to the currently used method of administering free imaging agent. An even smaller metastasis of approximately 3 pixels (equivalent to a tumor of approximately 0.3 mm in diameter) was also detected using the complex of this invention, but was not detectable by the free gad-d (FIG. 14A-14D).

Figure 16:
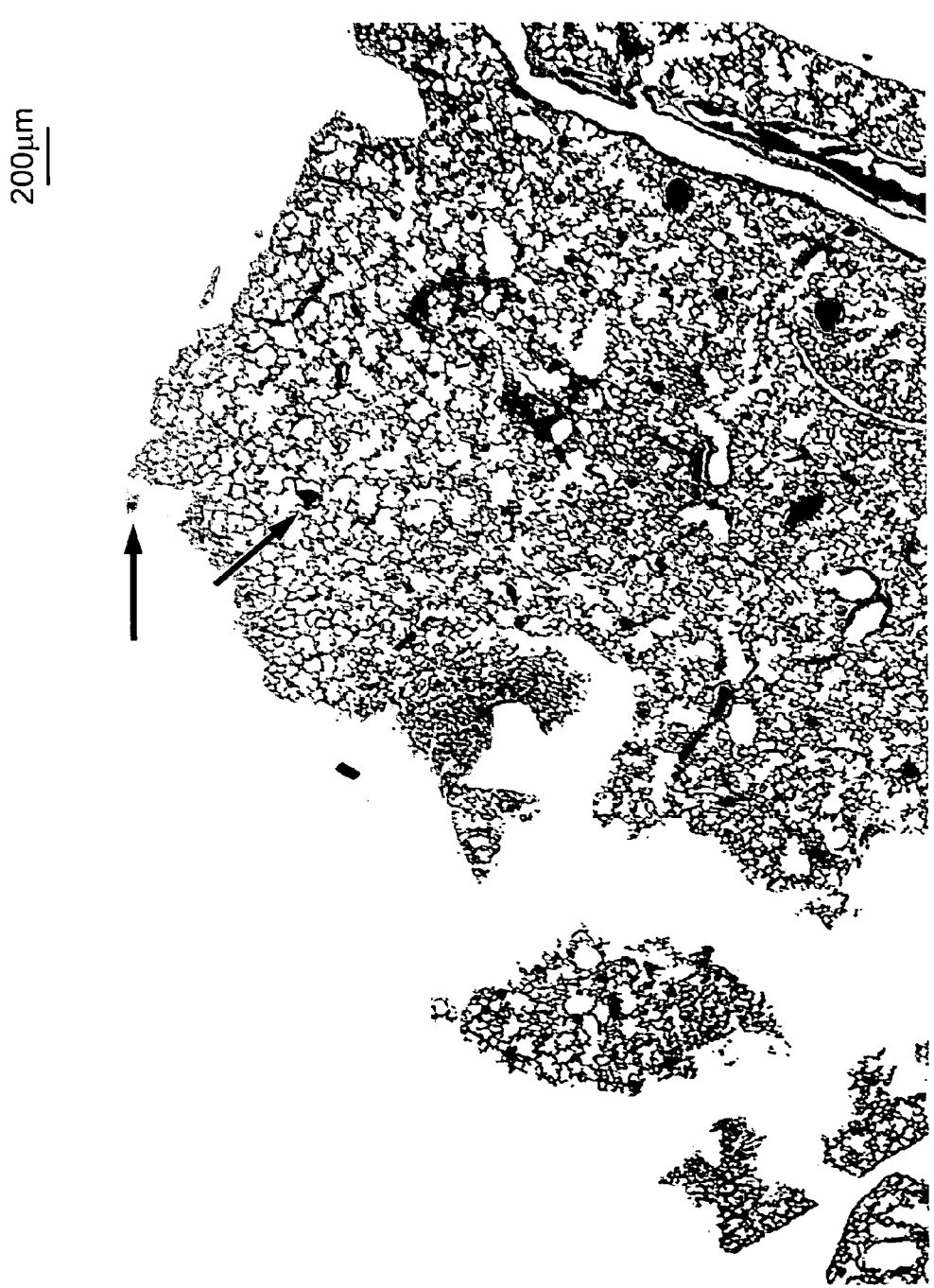
FIG. 16 shows sections of metastatic tissue confirming the detection/imaging seen by MRI using the Mag-comprising complexes of the present invention.
Figure 17:
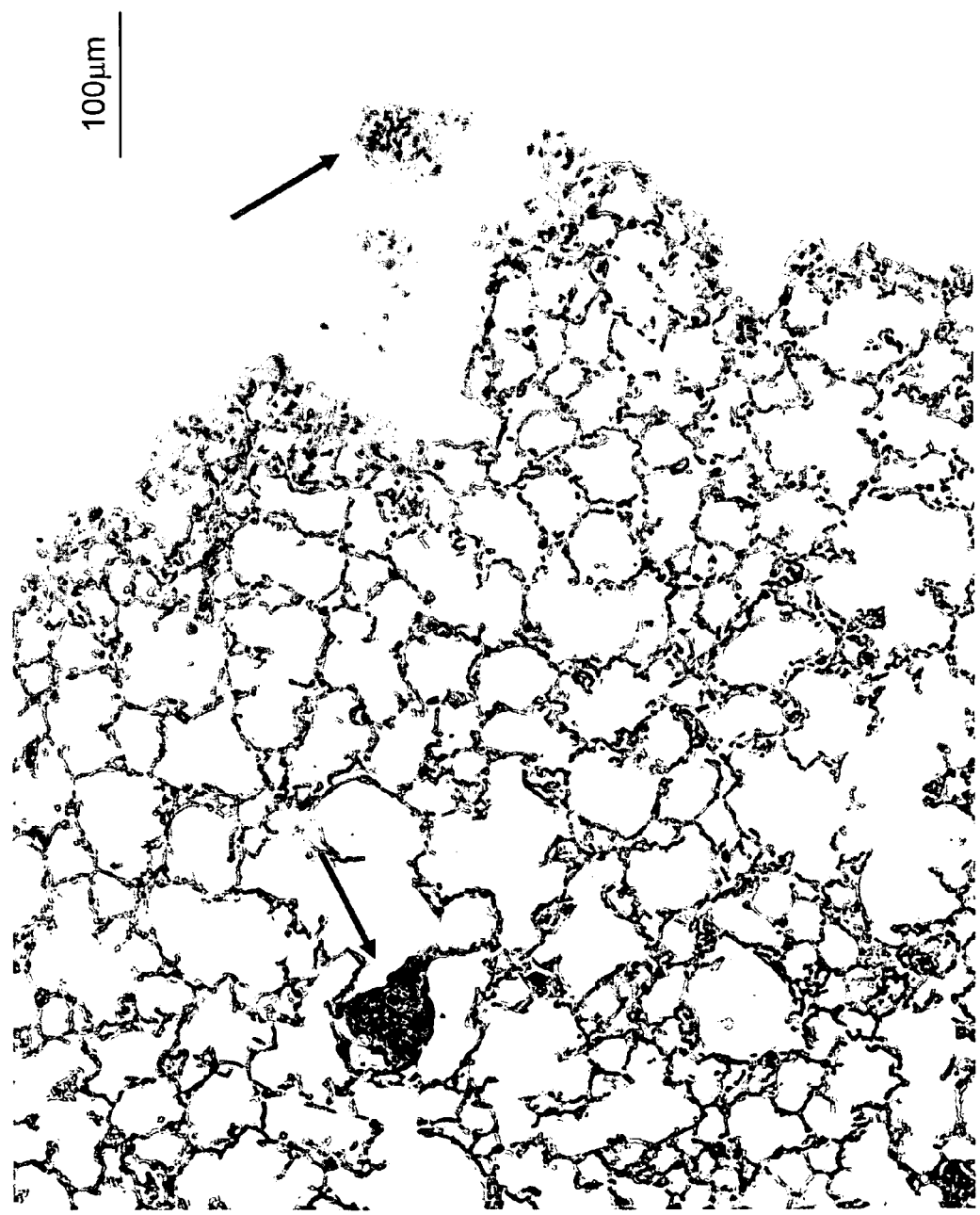
FIG. 17 shows higher magnification of FIG. 16.

Employing the identical tumor model system as above, tumors of even smaller size can be detected after intravenous injection of the complex of the invention. Here the imaging parameters used were also T1-weighted 2D (2-dimensional) Mutltislice-Multiecho imaging sequence, TE 10.21 ms, with TR=630.8ms, Flipback off, 8 averages with a field of view of 2.56×2.56 cm and a 256×256 matrix. As shown in FIG. 15A-15B, nodules of 1-2 pixels were detectable by the complex. Nodules N1 and N2 were visualized on the MRI scan. As they are so small (1-2 pixels) to determine if they were actually giving signal above background, intensity was measured using Image J software and the minimum, maximum, mean values and standard deviation (SD) was determined for the two nodules. Statistically, if the max of the nodule was greater than the max of the base +2SD of the base, there is a 95% confidence that the nodule is not noise but is real. Nodule 2 is clearly within this 95% confidence and Nodule 1 is just at the limit, thus it too is most likely a real tumor mass enhanced by the complex. After imaging the lungs from this animal were removed, fixed in Formalin, paraffin embedded, sectioned and stained using H&E using standard procedures well know to one of ordinary skill in the art. The sections were examined by microscope and the observed metastasis photographed. As shown if FIG. 16 (low power, 2×) and FIG. 17 (high power, 10×), two metastases with a size of approximately 0.1 mm were found in the same lobe and approximate location as expected based upon the MRI. The distance between the two nodules was measured on the MRI image and was found to be equivalent (~600nm) to that based upon the histology. Thus, these extremely small histological determined tumor masses do in fact represent the nodules detected on MRI using the complex of this invention. The level of sensitivity of detection found here for lung metastases is greater than that currently seen with CT, the commonly used method of detection of primary tumors of the lung and lung metastases derived from other cancer types. Clearly this represents and unexpected and surprising result.

EXAMPLE 7

Detection of Sub-Pleural Lung Metastases by TJRscFv-Lip-Magnevist

Employing the identical tumor model system and imaging parameters as described above in Example 6 above for FIGS. 13 and 14, it is also possible to detect metastases in the sub pleura of the lung as shown in FIG. 18A-18F. This is unexpected and surprising since current MRI imaging with non-complexed agents which do not actually enter the cell are not able to detect metastases in this location. This provides a significant advantage in early detection and treatment of lung and other types of cancer.

EXAMPLE 8

Enhanced Detection of Melanoma Lung Metastasis by TJRscFv-Lip-Magnevist

With respect to detection/treatment of pleural metastases, clinical control is very difficult to achieve and measurement of benefit is also difficult. The results presented in the Examples herein indicate that the complexes of this invention can reach and transfect pleural metastases and therefore can also be used to treat them. Moreover, the complexes of this invention could be the imaging tool employed to measure effectiveness of this, or any other therapy.

The following experiments were performed to demonstrate that when administered intravenously (or via any other appropriate route, e.g., but not limited to IT, ID, IM, IP) the complexes of the present invention carrying an imaging agent can detect metastases that are not limited to those from renal cell carcinomas. Lung tumors were induced in female C57/B1 6 mice by the intravenous injection of 0.1 to $5 \times 10^5$ B16/F10 mouse melanoma cells. This method results in metastases that reside almost exclusively in the lungs of the animals and thus serves as a model system for any type of cancer that results in lung tumors either as primary disease or as metastases. Approximately 2-4 weeks later, the animals were used for imaging.

Cationic liposome (DOTAP:DOPE) was prepared by the ethanol injection method as previously described (see U.S. Published Patent Application No. 2003/0044407; Xu L, et al., *Molecular Cancer Therapeutics* 1:337-346 (2002) the disclosures of each of which are incorporated herein by reference). The targeting moiety used in these studies is the anti-transferrin receptor single chain antibody fragment (TfRscFv).

To encapsulate the imaging agent, the TfRscFv was mixed with the liposome at a specific ratio and incubated at room temperature for 1-30 minutes, suitably 5-20 minutes, most suitably 10-12 minutes. Magnevist® was added to this solution, mixed and again incubated at room temperature for 1-30 minutes, suitably 5-20 minutes, most suitably 10-12 minutes. When prepared for in vivo use, sucrose or dextrose was added to a final concentration of 0.5-50%, suitably 1-20%, most suitably 10% for sucrose and 5% for dextrose, and incubated at room temperature for 1-30 minutes, suitably 5-25 minutes, most suitably 15-20 minutes. The complex is formed at a ratio of 1 mg imaging agent to 0.33-1.17 ug TfRscFv to 10-35 ug Liposome (suitably 1 mg imaging agent to 0.5 to 1.0 ug TfRScFv to 14-28 ug Liposome, most suitably 1 mg imaging agent to 0.71 ug TfRscFv to 21 ug Liposome) using the above procedure. A range of acceptable sizes of the complex is from about 20 to 1000 nm, suitably 50 to 70 nm and most suitably 100 to 500 nm. Here the complex was formed using 4.7 mg Magnevist, 99 ug Liposome and 3.3 ug TfRscFv with dextrose to a final concentration of 5%.

A mouse bearing lung tumors induced above was anesthetized and placed in an animal holder system. Anesthesia was induced using isoflurane at 4%, with the remaining gas comprising a 66% oxygen and 30% nitrous oxide mixture. Maintenance of anesthesia was achieved with 1.0 to 2.0% isoflurane (preferably 1.5%) under similar gaseous conditions of oxygen and nitrous oxide as noted. The anesthetized animal was positioned inside of a cylindrical variable radiofrequency resonant antenna (bird cage resonator volume coil) and tuned to a center frequency of approximately 300 MHz (the resonant frequency of water molecules when subject to a field strength of 7 Tesla). The imaging protocol used was T1-weighted two dimensional Turbo Multislice-Multiecho imaging sequence performed on a 7T Bruker BioSpin (Germany/USA) imaging console. The imaging parameters used were: T1-weighted 2D (2-dimensional) imaging sequence, TE 10.21 ms, TR 1418.13ms, Flipback off, 8 averages with a field of view of 3.84 x 3.84 cm and a 256×256 matrix. After a baseline image was acquired, the animal was kept immobilized in the animal holder and either the free (uncomplexed) Magnevist® (gad-d) or the TfRscFv-Lip-Mag complex containing the identical amount of Mag (total volume 50-1000 ul, suitably 100-500 ul, most suitably 200-400 ul) was systemically administered using a 27G needle by intravenous injection into the tail vein of the animal and the imaging sequence was immediately initiated. The pixel intensity of the images was measured. The same mouse was used for imaging with both the free and the complex. The imaging was performed on sequential days.

Figure 19B:
FIG. 19A-19B shows detection of $B_{16}/F_{10}$ melanoma lung metastases by Mag-comprising complexes of the present invention.
Figure 19A:
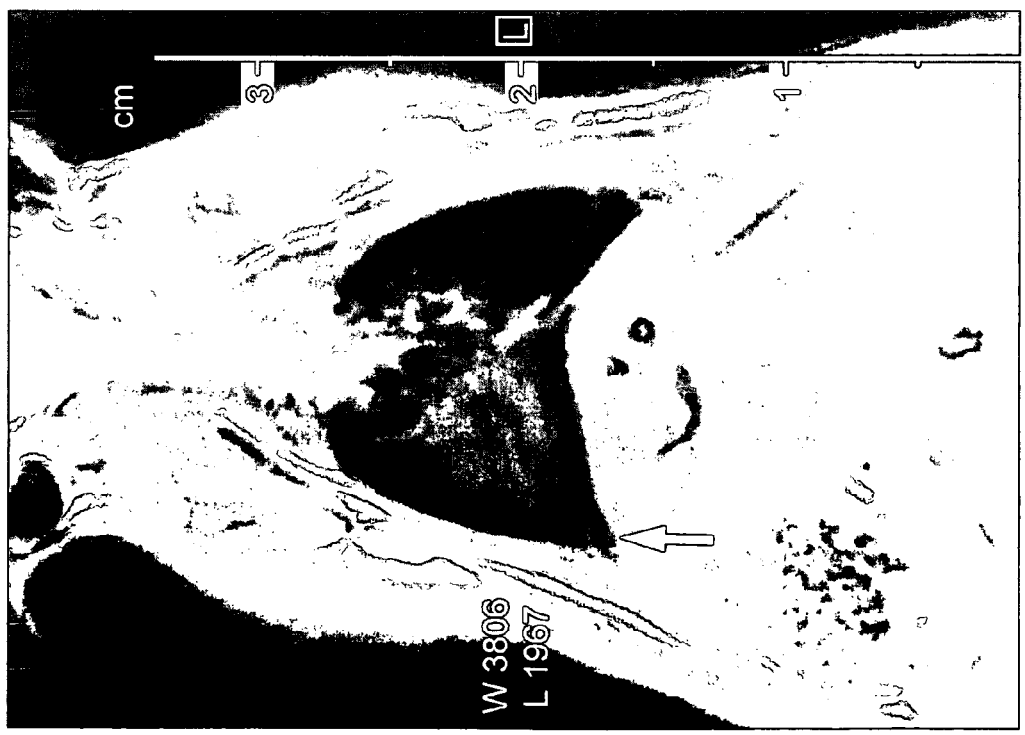

As Shown in FIG. 19A-19B, two small metastases (arrows) were detected in the lungs after injection with the complexed Magnevist® (Mag). The images represent two different slices through the lungs.

Employing the identical tumor model system (B16/F10 melanoma) and imaging parameters as above, pixel intensity of a metastasis in another animal was measured using dynamic profiling in Image J software after baseline, after Free Magnevist® and after TfRscFv-Lip-Mag and the values compared. As shown in Table 4 below, the complex showed the greatest enhancement over the baseline value. The Standard Deviation shows that the difference between complex and baseline values is significant while that between Free Magnevist® and baseline is not.

TABLE 4

Comparison of Signal Intensities in a B16/F10 Lung Metastasis

| Treatment | Maximum Pixel Value | Average Pixel Value | Standard Deviation |
|---|---|---|---|
| Baseline ® | 12888 | 7765.1 | 1757.2 |
| Free Magnevist ® | 17959 | 12979.3 | 2976.8 |
| Complexed Magnevist ® | 22351 | 14341.3 | 2384.6 |

References

1. Gillies, R. J., et al., *Neoplasia (New York)* 2:139-451 (2000)
2. Degani, H., et al., *Thrombosis & Haemostasis* 89:25-33 (2003)
3. Xu, L., et al., *Human Gene Therapy* 10:2941-2952 (1999)
4. Xu, L., et al., *Tumor Targeting* 4:92-104 (1999)
5. Xu,L., et al., *Molecular Medicine* 7:723-734 (2001)
6. Xu L, et al., *Molecular Cancer Therapeutics* 1:337-346 (2002)
7. Rait, A., et al., *Molecular Medicine* 8:476-487 (2002)
8. Rait, A., et al., *Ann. N.Y Acad. Sci.* 1002:1-12 (2003)
9. Cristiano, R. J., and Curiel, D. T., *Cancer Gene Therapy* 3:49-57 (1996)
10. Cheng, P. W., *Human Gene Therapy* 7:275-282 (1996)
11. Keer, H. N., et al., *Journal of Urology* 143:381-385 (1990)
12. Rossi, M. C., and Zetter, B. R., *Proc. Natl. Acad. Sci. (USA)* 89:6197-6201 (1992)
13. Elliott, R. L., et al., *Ann. N.Y Acad. Sci.* 698:159-166 (1993)
14. Thorstensen, K., and Romslo, I., *Scand. J. Clin. Lab. Investig. (Supp)* 215:113-120 (1993)
15. Miyamoto, T., et al., *Int'l. J. Oral Maxillofacial Surg.* 23:430-433 (1994)
16. Ponka, P. and Lok, C. N., *Int'l. J. Biochem. Cell Biol.* 31:1111-1137 (1999)
17. Haynes, B. F., et al., *J. Immunol.* 127:347-351 (1981)
18. Batra, J. K., et al., *Molecular & Cellular Biology* 11:2200-2205 (1991)
19. Jain, R. K. and Baxter, L. T., *Cancer Res.* 48:7022-7032 (1988)
20. Wolfert, M. A., et al., *Human Gene Therapy* 7:2123-2133 (1996)
21. Dunlap, D. D., et al., *Nucleic Acids Research* 25:3095-3101 (1997)
22. Kawaura, C., et al., *FEBS Letters* 421:69-72 (1998)
23. Choi, Y. H., et al., *Human Gene Therapy* 10:2657-2665 (1999)
24. Diebel, C. E., et al., *Nature* 406:299-302 (2000)
25. Rasa, M., et al., *J. Coll. Interface Sci* 250:303-315 (2002)
26. Yu, W., et al., *Nucleic Acids Research,* 32(5):e48(2004)
27. Alisauskus, R., et al., *Cancer Research* 55:5743s-5748s (1995)
28. Foo, J. J., et al., *Annals of Biomedical Engineering* 31:1279-1286 (2003)
29. Xu, L, et al., *Human Gene Therapy* 13:469-481 (2002)
30. Freedman, M., et al., *SPIE Medical Imaging: Physiology and Function from Multidimensional Images* 4321:163-167 (2001)
31. Wisner, E. R., et al., *Investigative Radiology* 37:232-239 (2002)
32. Winter, P. M., et al., *Circulation* 108:2270-2274 (2003)
33. Morawski, A. M., et al., *Magnetic Resonance in Medicine* 51:480-486 (2004)

All publications, patents and patent applications mentioned in this specification are herein inc-orporated by reference to the same extent as if each individual publication, patent or patent application was specifically and individually indicated to be incorporated by reference.

What is claimed is:

1. A method of imaging an organ or a tissue in a patient comprising:
   1) administering to the patient prior to performing said imaging an antibody- or antibody fragment-targeted cationic immunoliposome complex comprising:
      a) a cationic liposome,
      b) an antibody or antibody fragment which binds to a receptor that is differentially expressed on a target cell, and
      c) an imaging agent,
   wherein said antibody- or antibody fragment-targeted cationic immunoliposome complex was prepared by:
      i) preparing a cationic immunoliposome comprising said antibody or antibody fragment and said cationic liposome, wherein said antibody or antibody fragment is not chemically conjugated to said cationic liposome, and
      ii) mixing said cationic immunoliposome with said imaging agent at a ratio in the range of about 1.0:10 to about 1.0:35 (mg imaging agent:µg liposome); and
   2) imaging said organ or said tissue.

2. The method of claim 1, wherein said administration comprises intravenous administration, intramuscular administration, intradermal administration, intraocular administration, intraperitoneal administration, intratumoral administration, intranasal administration, intracereberal administration or subcutaneous administration.

3. The method of claim 1, wherein said tissue is a cancerous tissue.

4. The method of claim 3, wherein said cancerous tissue is a cancerous metastasis.

5. The method of claim 3, wherein said administration comprises intravenous administration, intramuscular administration, intradermal administration, intraocular administration, intraperitoneal administration, intratumoral administration, intranasal administration, intracereberal administration or subcutaneous administration.

6. The method of claim 4, wherein said administration comprises intravenous administration, intramuscular administration, intradermal administration, intraocular administration, intraperitoneal administration, intratumoral administration, intranasal administration, intracereberal administration or subcutaneous administration.

7. A method of imaging and treating a cancerous tissue in a patient suffering from cancer comprising:
   1) administering to the patient an antibody- or antibody fragment-targeted cationic immunoliposome complex comprising:
      a) a cationic liposome,
      b) an antibody or antibody fragment which binds to a receptor that is differentially expressed on a cancer cell, and
      c) an imaging agent,
   wherein said antibody-or antibody fragment-targeted cationic immunoliposome complex was prepared by:
      a) preparing a cationic immunoliposome comprising said antibody or antibody fragment and said cationic liposome, wherein said antibody or antibody fragment is not chemically conjugated to said cationic liposome and
      b) mixing said cationic immunoliposome with said imaging agent at a ratio in the range of about 1.0:10 to about 1.0:35 (mg imaging agent:µg liposome);
   2) imaging said cancerous tissue; and
   3) administering an anti-cancer agent to the patient to treat the cancerous tissue.

8. The method of claim 7, wherein said administration comprises intravenous administration, intramuscular administration, intradermal administration, intraocular administration, intraperitoneal administration, intratumoral administration, intranasal administration, intracereberal administration or subcutaneous administration.

9. The method of claim 7, wherein said anti-cancer agent is a chemotherapeutic agent or small molecule.

10. The method of claim 9, wherein said chemotherapeutic agent is selected from the group consisting of docetaxel, mitoxantrone and gemcitabine.

11. The method of claim 9, wherein said anti-cancer agent is associated with said cationic immunoliposome.

12. The method of claim 7, wherein said anti-cancer agent is delivered before or after the cationic immunoliposome complex.

13. The method of claim 12, wherein said anti-cancer agent is delivered at least 12 hours before or after the cationic immunoliposome complex.

14. The method of claim 7, further comprising administering radiation therapy to the patient.

15. The method of claim 7, wherein said cancerous tissue is a cancerous metastasis.

16. The method of claim 1, wherein said imaging agent is a magnetic resonance imaging (MRI) agent, a computed tomography (CT) imaging agent, or a positron emission tomography (PET) imaging agent.

17. The method of claim 16, wherein said MRI agent is gadopentetate dimeglumine, iron oxide, or iopamidol, said CT imaging agent is barium or iodine, or said PET imaging agent is $^{18}$F-2-deoxy-2-fluoro-D-glucose (FDG).

18. The method of claim 3, wherein said imaging agent is a magnetic resonance imaging (MRI) agent, a computed tomography (CT) imaging agent, or a positron emission tomography (PET) imaging agent.

19. The method of claim 18, wherein said MRI agent is gadopentetate dimeglumine, iron oxide, or iopamidol, said CT imaging agent is barium or iodine, or said PET imaging agent is $^{18}$F-2-deoxy-2-fluoro-D-glucose (FDG).

20. The method of claim 4, wherein said imaging agent is a magnetic resonance imaging (MRI) agent, a computed tomography (CT) imaging agent, or a positron emission tomography (PET) imaging agent.

21. The method of claim 20, wherein said MRI agent is gadopentetate dimeglumine, iron oxide, or iopamidol, said CT imaging agent is barium or iodine, or said PET imaging agent is $^{18}$F-2-deoxy-2-fluoro-D-glucose (FDG).

22. The method of claim 7, wherein said imaging agent is a magnetic resonance imaging (MRI) agent, a computed tomography (CT) imaging agent, or a positron emission tomography (PET) imaging agent.

23. The method of claim 22, wherein said MRI agent is gadopentetate dimeglumine, iron oxide, or iopamidol, said CT imaging agent is barium or iodine, or said PET imaging agent is $^{18}$F-2-deoxy-2-fluoro-D-glucose (FDG).

24. The method of claim 1, wherein said mixing in ii) is at a ratio in the range of about 1:14 to about 1:28 (mg imaging agent:μg liposome).

25. The method of claim 14, wherein said mixing in ii) is at a ratio of about 1:21 (mg imaging agent:μg liposome).

26. The method of claim 7, wherein said mixing in b) is at a ratio in the range of about 1:14 to about 1:28 (mg imaging agent:μg liposome).

27. The method of claim 26, wherein said mixing in b) is at a ratio of about 1:21 (mg imaging agent:μg liposome).

* * * * *

SEQUENCE LISTING

<160> NUMBER OF SEQ ID NOS: 1

<210> SEQ ID NO 1
<211> LENGTH: 31
<212> TYPE: PRT
<213> ORGANISM: Artificial Sequence
<220> FEATURE:
<223> OTHER INFORMATION: Chemically synthesized - HoKC

<400> SEQUENCE: 1

```
Lys Lys His Lys Lys Lys Lys His Lys Lys Lys Lys His Lys Lys Lys
1               5                   10                  15

Lys His Lys Lys Lys Lys His Lys Lys Lys Lys His Lys Lys Cys
            20                  25                  30
```